United States Patent [19]

Zamboni et al.

[11] Patent Number: 5,506,227

[45] Date of Patent: Apr. 9, 1996

[54] PYRIDINE-SUBSTITUTED BENZYL ALCOHOLS AS LEUKOTRIENE ANTAGONISTS

[75] Inventors: Robert Zamboni, Point-Claire; Daniel Guay, Notre Dame De Ile Perrot; Jacques-Yves Gauthier, Laval, all of Canada

[73] Assignee: Merck Frosst Canada, Inc., Kirkland, Canada

[21] Appl. No.: 866,697

[22] Filed: Apr. 13, 1992

[51] Int. Cl.[6] .......... A61K 31/54; A61K 31/435; A61K 31/535; A61K 31/44; C07D 215/12; C07D 215/14; C07D 215/20; C07D 213/04; C07D 211/70; C07D 211/82; C07D 413/00; C07D 403/00

[52] U.S. Cl. .......... 514/227.8; 514/231.5; 514/233.5; 514/235.2; 514/235.8; 514/236.8; 514/237.2; 514/255; 514/277; 514/316; 514/318; 514/332; 514/335; 514/341; 514/342; 514/343; 514/351; 544/114; 544/124; 544/125; 544/128; 544/129; 544/133; 544/134; 544/137; 544/141; 544/146; 544/148; 544/149; 544/152; 544/158; 544/162; 544/163; 544/170; 544/171; 544/172; 544/174; 544/175; 544/358; 544/359; 544/363; 544/366; 544/369; 544/372; 544/379; 544/399; 544/400; 546/153; 546/159; 546/162; 546/168; 546/174; 546/175; 546/187; 546/194; 546/208; 546/209; 546/210; 546/214; 546/229; 546/230; 546/232; 546/233; 546/234; 546/235; 546/236; 546/237; 546/238; 546/240; 546/255; 546/256; 546/261; 546/264; 546/265; 546/266; 546/275; 546/276; 546/278; 546/280; 546/281; 546/284; 546/286; 546/290; 546/296; 546/301; 546/302; 546/329; 546/330; 546/334; 546/339; 546/340; 546/341

[58] Field of Search .......... 546/342, 174, 546/153, 159, 162, 168, 175, 187, 194, 208, 209, 210, 214, 229, 230, 232, 233, 234, 235, 236, 237, 238, 240, 255, 256, 261, 264, 265, 266, 275, 276, 278, 280, 281, 284, 286, 290, 296, 301, 302, 329, 330, 334, 339, 340, 341; 544/114, 124, 125, 128, 129, 133, 134, 137, 141, 146, 148, 149, 152, 158, 162, 163, 170, 171, 172, 174, 175, 358, 359, 363, 366, 369, 372, 379, 399, 403; 514/227.8, 231.5, 233.5, 235.8, 237.2, 255, 277, 316, 318, 332, 335, 341, 342, 343, 357

[56] References Cited

U.S. PATENT DOCUMENTS 4,760,068  7/1988  Terao et al. .......... 540/347
5,004,743  4/1991  Young et al. .......... 514/227.8

FOREIGN PATENT DOCUMENTS

0110405A2  11/1983  European Pat. Off. .
0181568A2  10/1985  European Pat. Off. .
0318093   5/1989   European Pat. Off. .
0480708A2  10/1991  European Pat. Off. .
WO89/12629  12/1989  WIPO .

OTHER PUBLICATIONS

*Chemical Abstract*, vol. 117 No. 131085p, 1992, Belley et al, "Preparation of Saturated Hydroxyalkylquinolines Acids as Leukotiene Antagonists.".

*Primary Examiner*—C. Warren Ivy
*Assistant Examiner*—Raymond Covington
*Attorney, Agent, or Firm*—Mollie M. Yang; David L. Rose

[57] ABSTRACT

Compounds having the formula I:

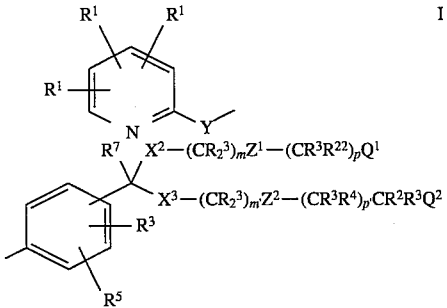

are antagonists of the actions of leukotrienes. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

4 Claims, No Drawings

PYRIDINE-SUBSTITUTED BENZYL ALCOHOLS AS LEUKOTRIENE ANTAGONISTS

BACKGROUND OF THE INVENTION

The leukotrienes constitute a group of locally acting hormones, produced in living systems from arachidonic acid. The major leukotrienes are Leukotriene $B_4$ (abbreviated at $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis, as well as the metabolism of the leukotrienes, are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

U.S. Pat. No. 5,004,743 discloses structures of leukotriene antagonists which differ from the present compounds, most notably in the absence of the benzyl alcohol and of fused cycloalkyl pyridines. The structure of the compounds disclosed in the above patent application is shown below.

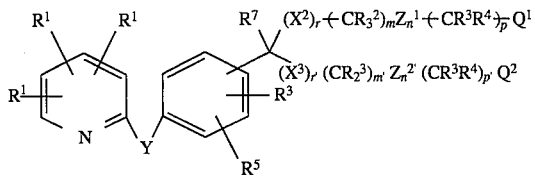

U.S. PAT. NO. 5,004,473

The art also describes certain quinoline-containing compounds as having leukotriene antagonist activity. Thus, EP 318,093 (Merck) describes compounds of structure A while compounds of structure B are disclosed in WO 89/12629 (Rorer).

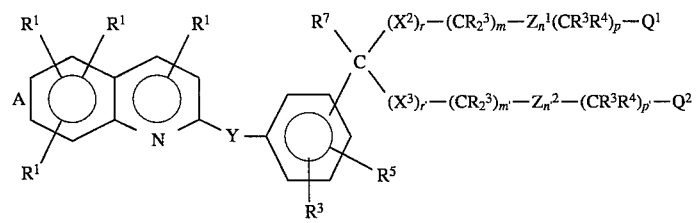

EP 318,093 (Merck)

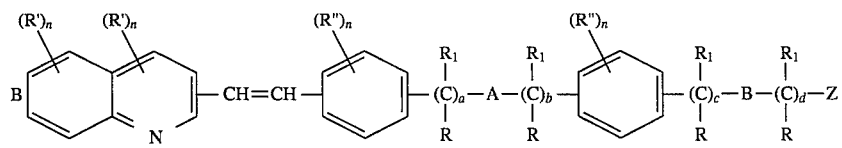

WO 89/12629 (Rorer)

SUMMARY OF THE INVENTION

The present invention relates to pyridine-substituted benzyl alcohols having activity as leukotriene antagonists, to methods for their preparation, and to methods and pharmaceutical formulations for using these compounds in mammals (especially humans).

Because of their activity as leukotriene antagonists, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

DETAILED DESCRIPTION OF THE INVENTION

The compounds of this invention are best realized by Formula I:

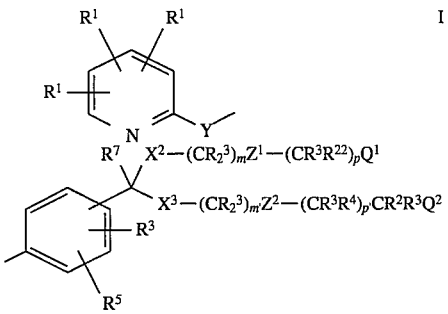

wherein:

$R^1$ is H, halogen, CN, lower alkyl, cyloalkyl, polyhalo lower alkyl, lower alkoxy, lower alkoxy lower alkyl, lower alkylthio lower alkyl, lower alkenyl, substituted or unsubstituted phenyl, pyridyl, thiazolyl, oxazolyl, furanyl or thienyl, or adjacent $R^1$'s and the carbons through which they are attached may form a saturated ring of 5 to 10 carbon atoms;

$R^2$ is lower alkyl, lower alkenyl, lower alkynyl, —$CF_3$, —$CH_2F$, —$CHF_2$, —$CH_2CF_3$, substituted or unsubstituted phenyl, substituted or unsubstituted benzyl, substituted or unsubstituted 2-phenethyl, or two $R^2$ groups joined to the same carbon may form a saturated ring of up to 8 members containing 0 to 2 heteroatoms chosen from O, S, and N;

$R^3$ is H or $R^2$;

$CR^3R^{22}$ may be the radical of a standard amino acid;

$R^4$ is halogen, —$NO_2$, —CN, —$OR^3$, —$SR^3$, $NR^3R^3$, $NR^3C(O)R^7$, or $R^3$;

$R^5$ is H, halogen, —$NO_2$, —$N_3$, —CN, —$SR^2$ —$NR^3R^3$, —$OR^3$, lower alkyl, or —$C(O)R^3$;

$R^6$ is —$(CH_2)_s$—$C(R^7R^7)$—$(CH_2)_s$—$R^8$ or —$CH_2C(O)NR^{12}R^{12}$;

$R^7$ is H or lower alkyl;

$R^8$ is
A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
B) the radical W—$R^9$;

$R^9$ contains up to 20 carbon atoms and is (1) an alkyl group or (2) an alkylcarbonyl group of an organic acyclic or monocyclic carboxylic acid containing not more than 1 heteroatom in the ring;

$R^{10}$ is —$SR^{11}$, —$OR^{12}$, or —$NR^{12}R^{12}$;

$R^{11}$ is lower alkyl, —$C(O)R^{14}$, unsubstituted phenyl, or unsubstituted benzyl;

$R^{12}$ is H, $R^{11}$, or two $R^{12}$ groups joined to the same N may form a saturated ring of 5 or 6 members containing up to two heteroatoms chosen from O, S, and N;

$R^{13}$ is lower alkyl, lower alkenyl, lower alkynyl, —$CF_3$, or substituted or unsubstituted phenyl, benzyl, or 2-phenethyl;

$R^{14}$ is H or $R^{13}$;

$R^{15}$ is $R^3$ or halogen;

$R^{16}$ is H, lower alkyl, or OH;

$R^{17}$ is lower alkyl, lower alkenyl, lower alkynyl, or substituted or unsubstituted phenyl, benzyl, or 2-phenethyl;

$R^{18}$ is lower alkyl, lower alkenyl, lower alkynyl, —$CF^3$, or substituted or unsubstituted phenyl, benzyl, or 2-phenethyl;

$R^{19}$ is lower alkyl, lower alkenyl, lower alkynyl, —$CF^3$, or substituted or unsubstituted phenyl, benzyl, or 2-phenethyl;

$R^{20}$ is H, lower alkyl, substituted or unsubstituted phenyl, benzyl, phenethyl, or pyridinyl, or two $R^{20}$ groups joined to the same N may form a saturated ring of 5 or 6 members containing one to two heteroatoms chosen from O, S, and N;

$R^{21}$ is H or $R^{17}$;

$R^{22}$ is $R^4$, $CHR^7OR^3$, or $CHR^7SR^2$;

m and m' are independently 0–8;

p and p' are independently 0–8;

m+p is 1–10 when $X^2$ is O, S, S(O), or $S(O)_2$;

m+p is 0–10 when $X^2$ is $CR^3R^{16}$ or a bond;

m'+p' is 0–10;

s is 0–3;

$Q^1$ is —$C(O)OR^3$, 1H (or 2H)-tetrazol-5-yl, —$C(O)OR^6$, —$C(O)NHS(O)_2R^{13}$, —CN, —$C(O)NR^{12}R^{12}$, $NR^{21}S(O)_2R^{13}$, —$NR^{12}C(O)NR^{12}R^{12}$, —$NR^{21}C(O)R^{18}$, $OC(O)NR^{12}R^{12}$, —$C(O)R^{19}$, —$S(O)R^{18}$, —$S(O)_2R^{18}$, —$S(O)_2NR^{12}R^{12}$, —$NO_2$, $NR^{21}C(O)OR^{17}$, —$C(NR^{12}R^{12})$=$NR^{12}$, or —$C(R^{13})$=NOH; or if $Q^1$ is C(O)OH and $R^{22}$ is —OH, —SH, $CHR^7OH$ or —$NHR^3$, then $Q^1$ and $R^{22}$ and the carbons through which they are attached may form a heterocyclic ring by loss of water;

$Q^2$ is $OR^3$;

W is O, S, or $NR^3$;

$X^1$ is O, S, —S(O)—, —$S(O)_2$—, —$N(R^3)$—, or —$CR^3R^3$—;

$X^2$ and $X^3$ are independently O, S, S(O), $S(O)_2$, $CR^3R^{16}$, or a bond;

Y is —$CR^3$=$CR^3$—, —C≡C—, —$CR^3R^3$—$X^1$—, —$X^1$—$CR^3R^3$—, —$CR^3R^3$—$X^1$—$CR^3R^3$—, —C(O)—, —$NR^3C(O)$—, —$C(O)NR^3$—, O, S, $NR^3$, or

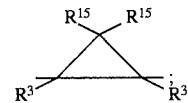

$Z^1$ and $Z^2$ are independently —HET(—$R^3$—$R^5$)— or a bond;

HET is the diradical of a benzene, a pyridine, a furan, or a thiophene;

or a pharmaceutically acceptable salt thereof.

More preferred compounds of Formula I are represented by Formula Ia:

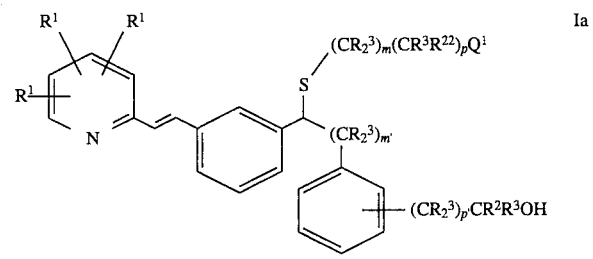

wherein:

$R^1$ is H, halogen, lower alkyl, polyhalo lower alkyl, lower alkoxy or adjacent $R^1$'s and the carbons through which they are attached may form a saturated ring of 5 to 7 carbon atoms;

$R^{22}$ $R^3$, —$CH_2OR^3$, or —$CH_2SR^2$;

$Q^1$ is —C(O)OH, 1H(or 2H)-tetrazol-5-yl, —$C(O)NHS(O)_2R^{13}$, —$C(O)NR^{12}R^{12}$, or —$NHS(O)_2R^{13}$;

m' is 2 or 3;

p' is 0 or 1;

m+p is 1–5; and the remaining definitions are as in Formula I; or a pharmaceutically acceptable salt thereof.

The following abbreviations have the indicated meanings:

AIBN=2,2'-azobis(isobutyronitrile)
Py=2-, 3-, or 4-pyridyl
Fu=2- or 3-furanyl
Et=ethyl
Me=methyl
Bz=benzyl
Ph=phenyl
t-Bu=tert-butyl
i-Pr=isopropyl
n-Pr=normal propyl
c-Hex=cyclohexyl
c-Pr=cyclopropyl
c-=cyclo
Ac=acetyl
Tz=tetrazol-5-yl
Th=2- or 3-thienyl C₃H₅=allyl
i-C₃H₅=2-propenyl
c-Pen=cyclopentyl
c-Bu=cyclobutyl
PPTS=pyridinium p-toluene sulfonate
phe=benzenediyl
NBS=N-bromosuccinimide
NCS=N-chlorosuccinimide
pye=pyridinediyl
PTSA=p-toluenesulfonic acid
Thia=thiazolyl
Ox=oxazolyl
fur=furandiyl
r.t.=room temperature
thio=thiophenediyl
DHP=4H-2,3-dihydropyran
THP=tetrahydropyran The terms alkyl, alkenyl, and alkynyl mean linear and branched structures and combinations thereof.

The term "alkyl" includes "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

The term "polyhalo" means one or more hydrogen atoms are replaced by halogen atoms.

The term "lower alkyl" means alkyl groups of from 1 to 7 carbon atoms. Examples of lower alkyl groups include methyl, ethyl, propyl, isopropyl, butyl, s- and t-butyl, pentyl, hexyl, heptyl, and the like.

The term "polyhalo lower alkyl" means a lower alkyl group in which one or more of the hydrogen atoms has been replaced by a halogen atom.

The term "cycloalkyl" refers to a hydrocarbon, containing one or more rings of from 3 to 12 carbon atoms, with the hydrocarbon having up to a total of 20 carbon atoms. Examples of cycloalkyl groups are cyclopropyl, cyclopentyl, cycloheptyl, aldamantyl, cyclododecylmethyl, 2-ethyl-1-bicyclo[4.4.0]decyl, and the like.

The term "alkenyl" includes "lower alkenyl" and means alkenyl groups of 2 to 20 carbon atoms. Examples of alkenyl groups include allyl, 5-decen-1-yl, 2-dodecen-1-yl, and the like.

"Lower alkenyl" means alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl, and the like.

"Cycloalkenyl" means alkenyl groups of 3 to 20 carbon atoms, which include a ring of 3 to 12 carbon atoms, and in which the alkenyl double bond may be located anywhere in the structure. Examples of cycloalkenyl groups are cyclopropen-1-yl, cyclohexen-3-yl, 2-vinyladamant-1-yl, 5-methylenedodec-1-yl, and the like.

The term "alkynyl" includes "lower alkynyl" and means alkynyl groups of 2 to 20 carbon atoms. Examples of alkynyl groups are ethynyl, 2-pentadecyn-1-yl, 1-eicosyn-1-yl, and the like.

"Lower alkynyl" means alkynyl groups of 2 to 7 carbon atoms. Examples of lower alkynyl groups include ethynyl, propargyl, 3-methyl-1-pentynyl, 2-heptynyl, and the like.

The term "cycloalkynyl" means alkynyl groups of 5 to 20 carbon atoms, which include a ring of 3 to 20 carbon atoms. The alkynyl triple bond may be located anywhere in the group, with the proviso that if it is within a ring, such a ring must be of 10 members or greater. Examples of cycloalkynyl are cyclododecyn-3-yl, 3-cyclohexyl-1-propyn-1-yl, and the like.

The term "lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

The term "lower alkylthio" means alkylthio groups of from 1 to 7 carbon atoms of a straight, branched or cyclic configuration. Examples of lower alkylthio groups include methylthio, propylthio, isopropylthio, cycloheptylthio, etc. By way of illustration, the propylthio group signifies —SCH₂CH₂CH₃.

The term "lower alkylsulfonyl" means alkylsulfonyl groups of from 1 to 7 carbon atoms of a straight, branched, or cyclic configuration. Examples of lower alkylsulfonyl groups are methylsulfonyl, 2-butylsulfonyl, cyclohexylmethylsulfonyl, etc. By way of illustration, the 2-butylsulfonyl group signifies —S(O)₂CH(CH₃)CH₂CH₃.

"Alkylcarbonyl" includes "lower alkylcarbonyl" and means alkylcarbonyl groups of 1 to 20 carbon atoms of a straight, branched, or cyclic configuration. Examples of alkylcarbonyl groups are 2-methylbutanoyl, octadecanoyl, 11-cyclohexylundecanoyl and the like. Thus, the 11-cyclohexylundecanoyl group is c-Hex—(CH₂)₁₀—C(O)—.

The term "lower alkylcarbonyl" means alkylcarbonyl groups of from 1 to 8 carbon atoms of a straight, branched, or cyclic configuration. Examples of lower alkylcarbonyl groups are formyl, 2-methylbutanoyl, cyclohexylacetyl, etc. By way of illustration, the 2-methylbutanoyl groups signifies —C(O)CH(CH₃)CH₂CH₃.

Substituted-phenyl, -benzyl, -2-phenethyl, or -pyridinyl means that the aromatic ring carries 1 or 2 substituents selected from lower alkyl, $R^{10}$, $NO_2$, $SCF_3$, halogen, —C(O)$R^7$, —C(O)$R^{10}$, CN, $CF_3$, and Tz.

Halogen includes F, Cl, Br, and I.

It is intended that the definitions of any substituent (e.g., $R^1$, $R^2$, $R^{10}$, etc.) in a particular molecule be independent of its definitions elsewhere in the molecule. Thus, —$NR^{12}R^{12}$ represents —NHH, —NHCH₃, —NHC₆H₅, etc.

The saturated rings formed when two $R^1$ groups join through two adjacent carbon atoms include c-pentane, c-hexane, c-heptane, c-octane, c-nonane, and c-decane.

The saturated rings formed when two $R^2$ groups join through C include c-propane, c-pentane, c-hexane, c-octane, tetrahydrofuran, tetrahydrothiophene, pyrrolidine, pyran, thiopyran, piperidine, dioxane, morpholine, thiomorpholine, piperazine, and their N-lower alkyl analogs.

The heterocycles formed when two $R^{12}$ or $R^{20}$ groups join through N include pyrrolidine, piperidine, morpholine, thiamorpholine, piperazine, and N-methylpiperazine.

When $Q^1$ and $R^{22}$ and the carbons through which they are attached form a ring, the rings thus formed include lactones, lactams, and thiolactones.

The prodrug esters of $Q^1$ (i.e., when $Q^1$=CO₂$R^6$) are intended to include the esters such as are described by Saari et al., J. Med. Chem., 21, No. 8, 746–753 (1978), Sakamoto et al., Chem. Pharm. Bull., 32, No. 6, 2241–2248 (1984), and Bundgaard et al., J. Med. Chem., 30, No. 3, 451–454 (1987).

Within the definition of $R^8$, some representative monocyclic or bicyclic heterocyclic radicals are:

2,5-dioxo-1-pyrrolidinyl, (3-Pyridinylcarbonyl)amino, 1,3-dihydro-1,3-dioxo-2H-isoindol-2-yl, 1,3-dihydro-2H-isoindol-2-yl, 2,4-imidazolinedion-1-yl, 2,6-piperidinedion-1-yl,
2-imidazolyl,
2-oxo-1,3-dioxolen-4-yl,
piperidin-1-yl,
morpholin-1-yl, and
piperazin-1-yl.

"Standard amino acid", the radical of which may be $CR^3R^{22}$, means the following amino acids: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine, and valine. See F. H. C. Crick, Symposium of the Society of Experimental Biology, 12, 140 (1958).

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof. Optically active (R) and (S) isomers may be resolved using conventional techniques.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Utilities

The ability of the compounds of Formula I to antagonize the actions of the leukotrienes makes them useful for preventing or reversing the symptoms induced by the leukotrienes in a human subject. This antagonism of the actions of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, myocardial ischemia, hypertension, platelet aggregation and the like, 7) renal insufficiency arising from ischaemia induced by immunological or chemical (cyclosporin) etiology, 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, and 15) cholecystitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatotoxic agents such as $CCl_4$ and D- galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory, or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaeutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional,pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combinations With Other Drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) propionic acid derivatives;
(2) acetic acid derivatives;
(3) fenamic acid derivatives;
(4) oxicams; and
(5) biphenylcarboxylic acid derivatives, or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

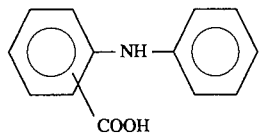

which can bear a variety of substituents and in which the free -COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

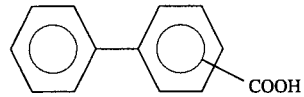

which can bear a variety of substituents and in which the free -COOH group can be in the form of a pharmaceutically acceptable salt group, e.g., —COO$^-$Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are nonnarcotic analgesics/non-steroidal anti-inflammatory drugs which have the general formula:

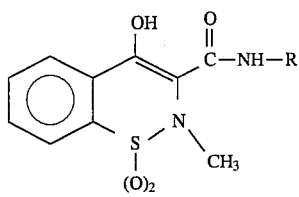

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., *Pharmaprojects*), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR$^{714}$, MR$^{897}$, MY309, 0N03144, PR$^{823}$, PV102, PV108, R$^{830}$, RS2131, SCR$^{152}$, SH440, SIR$^{133}$, SPAS510, SQ$^{27239}$, ST281, SY6001, TA60, TAI-901 (4-benzoyl-1- indancarboxylic acid), TVX2706, U60257, UR$^{2301}$, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172.(Jul. 21, 1982) and 61,800 (Jun. 10, 1982); and in U.K. Patent Specification No. 2,058, 785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an H$_1$- or H$_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terrenadine and like compounds, such as those disclosed in U.S. Pat. Nos. 4,283,408; 4,362,73 6; and 4,394,508. The pharmaceutical compositions may also contain a K$^+$/H$^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature*, 316, 126–131 (1985), and the like. Each of the references referred to in this paragraph is hereby incorporated herein by reference.

Other advantageous pharmaceutical compositions comprise the Formula I compounds in combination with anticholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Synthesis

Compounds of the present invention can be prepared according to the following methods.

Scheme 1

2-Methylpyridine of general structure III is prepared by α-methylation of substituted pyridine II using the method of Kray and Reinecke (J. Am. Chem. Soc., 1964, 86, 5355). Oxidation with m-chloroperbenzoic acid gives substituted 2-methylpyridine N-oxide IV. Treatment of the latter with phosphoryl chloride gives the 2-chloromethyl substituted pyridine VII. Alternatively, refluxing IV in acetic anhydride gives the 2-(acetoxymethyl) pyridine VII which is hydrolysed with aqueous base to the corresponding alcohol VII. When this hydroxymethyl derivative is treated with methanesulfonyl chloride in the presence of triethylamine, the 2-(methanesulfonyloxymethyl)pyridine is obtained, whereas treatment with brominetriphenylphosphine gives the 2-(bromomethyl)pyridine VII. When either the bromomethyl, chloromethyl, or the mesyloxymethyl pyridine derivative VII is refluxed in acetonitrile in the presence of triphenylphosphine, the corresponding phosphonium salt VIII is formed.

An alternative route to the 2-(hydroxymethyl) pyridine VII from variously substituted pyridine II involves (1) oxidation to the pyridine N-oxide, (2) a modified Reissert reaction according to the protocol of W. F. Fife (J. Org. Chem., 1983, 48, 1375) to give the 2-cyano pyridine VI, (3) conversion to the methyl ester with anhydrous methanol and acid, and (4) finally reduction of the 2-carbomethyoxypyridine with diisobutylaluminium hydride.

Scheme 2

2-Pyridinecarboxaldehydes such as IX (obtained by an oxidative procedure from VII or partial reduction of V1) can be deprotonated at the 6-benzylic position by successive treatment with lithium N,N,N-trimethylethylenediamine (LiTMEDA) and lithium diisopropylamide. Addition of an alkylating agent R'X gives the pyridine derivative X with an alkyl substituent at the 6-position. Reduction with sodium borohydride gives the carbinol XI which is then transformed into the phosphonium salt XII as described in Scheme 1.

Ramification of the 5-alkyl substituent of a 2-pyridinecarbonitrile XIII is done by treatment with a base such as potassium hexamethyldisilazide followed by an alkylating agent R"X to give XIV. The latter is converted to the phosphonium salt XV as described in Scheme 1.

Scheme 3

When treated with various organometallic reagents ($R^2M$), with or without catalyst, 2-halopyridines of general structure XVI give the corresponding 2-substituted pyridines XVII (such as in Example 2). The latter are also prepared by acylation of the pyridine N-oxide V followed by treatment with an organometallic reagent $R^2M$. Alternatively, condensation of enamines XVIII with an α,β-unsaturated carbonyl gives a dicarbonyl intermediate XIX which is cyclised to the pyridine XX with ammonia or an ammonium salt.

Scheme 4

Dialdehyde XXI is reduced with sodium borohydride. The resulting alcohol is protected as its tetrahydropyranyl ether XXII which is then treated with vinyl magnesium bromide or allyl magnesium bromide to give the alcohol XXIII. Coupling of XXIII with bromide XXIV in the presence of palladium acetate using the procedure of R. C. Larock et al. (Tetrahedron Letters, 30, 6629 (1989)) gives the keto ester XXV. The ketone is then reduced using the chiral oxazaborolidine complex with borane XXVI (J. Org. Chem., 56, 751, 1991) followed by reaction of the ester with an alkyl Grignard and cerium chloride to give the diol XXVII. (To obtain compound XXVII with one $R^2$=H cerium chloride is omitted, one equivalent of Grignard is used and the initally formed ketone is reduced to the corresponding benzyl alcohol.)

The chiral alcohol of the diol XXVII is first protected as its t-butyldimethylsilyl ether. The other benzylic alcohol is protected as a tetrahydropyranyl ether which is then treated with tetrabutylammonium fluoride to give the alcohol XXVIII. Mesylation of XXVIII followed by B displacement of the resulting mesylate with the appropriate substituted thiol XXIX gives the thioether XXX protected as a tetrahydropyranyl ether. The hydroxythioether XXX is obtained directly from diol XXVII by mesylation followed by thiol displacement.

Deprotection of the benzylic alcohol(s) of XXX and oxidation gives the benzaldehyde XXXI. Coupling of XXXI with VIII gives the olefin linked pyridine benzyl alcohol XXXII (I). In the case where $Q^1$ is an ester, hydrolysis with a base such as NaOH or LiOH (followed by acidification) affords the corresponding acid XXXII (I).

It will be obvious to one skilled in the art that compound XXXII (I) having the opposite stereochemistry at the sulfur-bearing benzylic carbon can be obtained by using the opposite enantiomer of the chiral reduction catalyst XXVI to reduce XXV to XXVII or by inversion of the stereocenter in XXVIII by a Mitsunobu reaction (Synthesis, 1–28, 1981).

Scheme 5

Reduction of ketoaldehyde XXXIII, followed by protection of the corresponding ketoalcohol as its tetrahydropyranyl ether gives XXXIV. The enolate of ketone XXXIV, obtained by treatment of XXXIV with a base such as KH or NaH, is reacted with dimethylcarbonate to yield the keto ester XXXV. Alkylation of the keto ester XXXV with iodide XXXVI followed by decarboxylation of the resulting adduct using conditions such as heating with HCl in acetic acid affords the ketone XXXVII. In the case where the THP ether is cleaved, the alcohol is reprotected as the THP ether. Following the procedure described in Scheme 4, ketone XXXVII is transformed to XXXVIII, a structure representative of I.

Scheme 6

Iodoacid XXXIX is treated with 2 equivalents of a base such as n-butyllithium in a suitable solvent such as THF at −100° C., then at −78° C. to afford XL, which is reacted with aldehyde XXI to yield the hydroxyacid XLI. The acid XLI is esterified using conditions such as $CH_2N_2$ or $CH_3I$/$Cs_2CO_3$ and an organometallic reagent is then added to give the diol XLII. Following the same procedure as in Scheme 4, the diol XLII is transformed to XLIII, which is a structure representative of I.

Scheme 7

Treatment of olefin-linked pyridine XXXII with trimethylsulfonium iodide gives the cyclopropyl-linked compound XLIV, which is a representative of I. Reduction of the olefin of XXXII with borane gives the saturated compound XLV, which is another representative of I.

Scheme 8

Starting from benzaldehyde derivative XLVI and following the same sequence as described in Scheme 4, XLVII is prepared, which is coupled with the halide VII to give the ether and the thioether linked pyridine XLVIII, which is a representative of I.

SCHEME 1

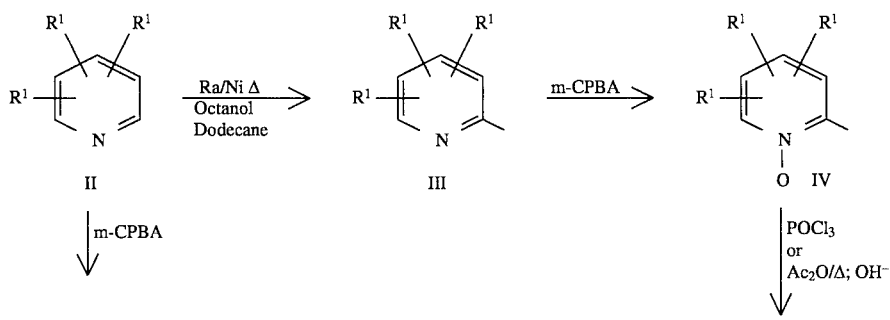

-continued
SCHEME 1
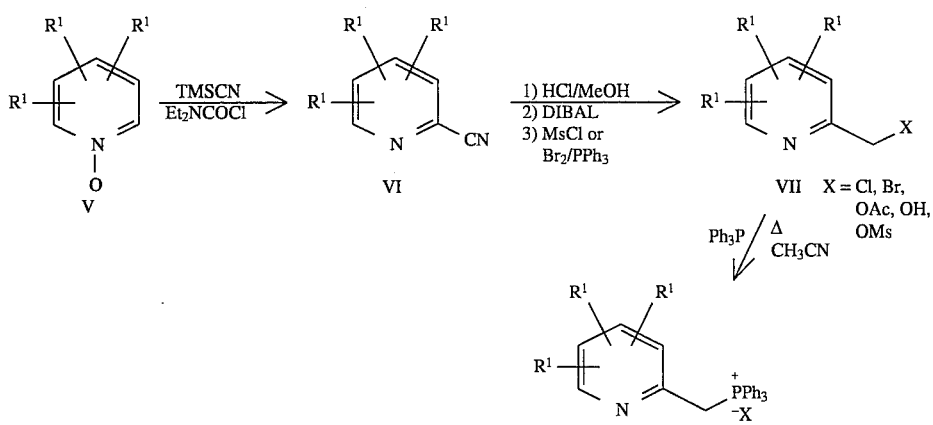
SCHEME 2
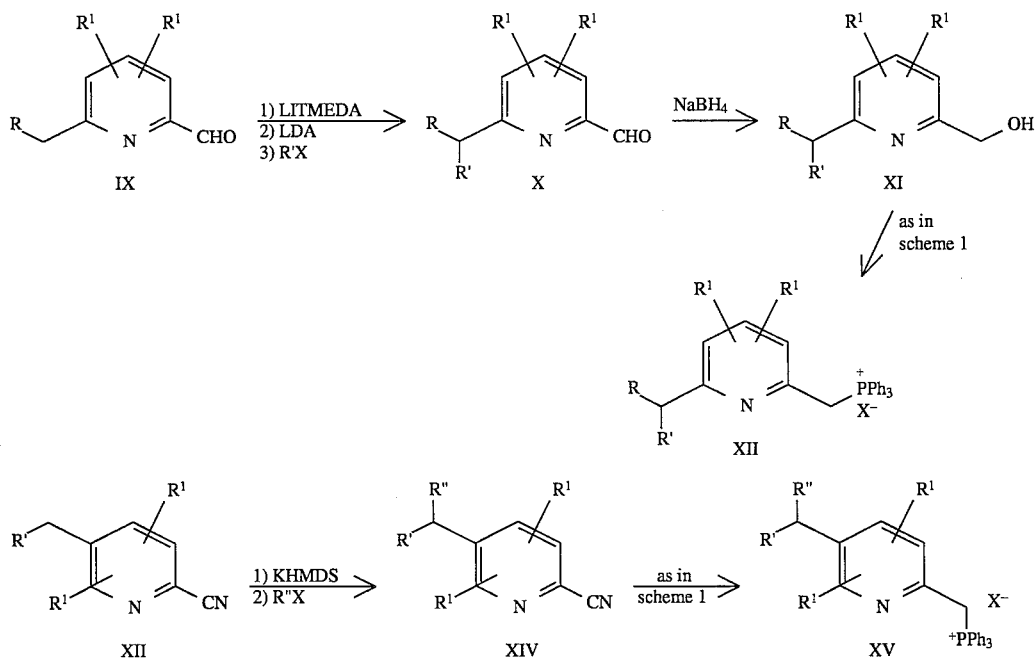
SCHEME 3
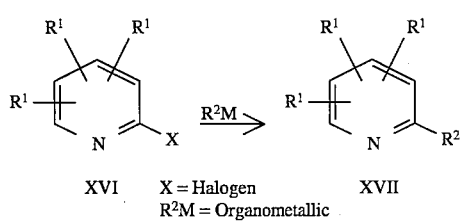

-continued
SCHEME 3
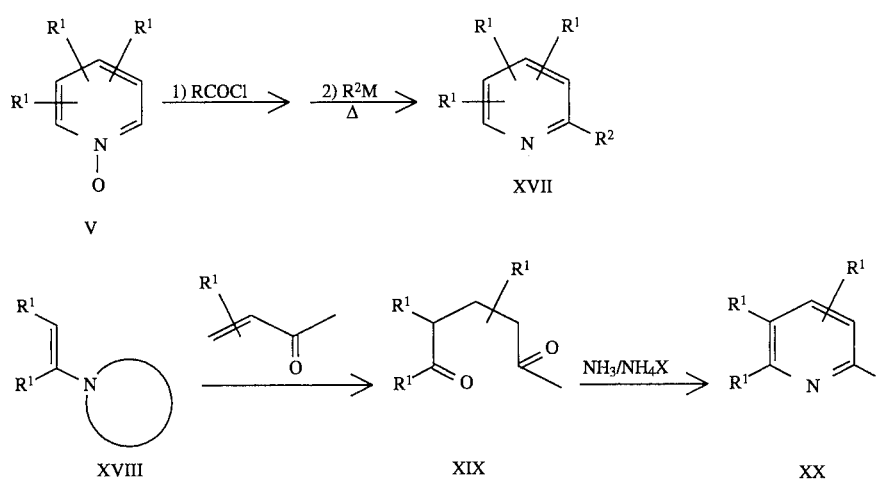

SCHEME 4
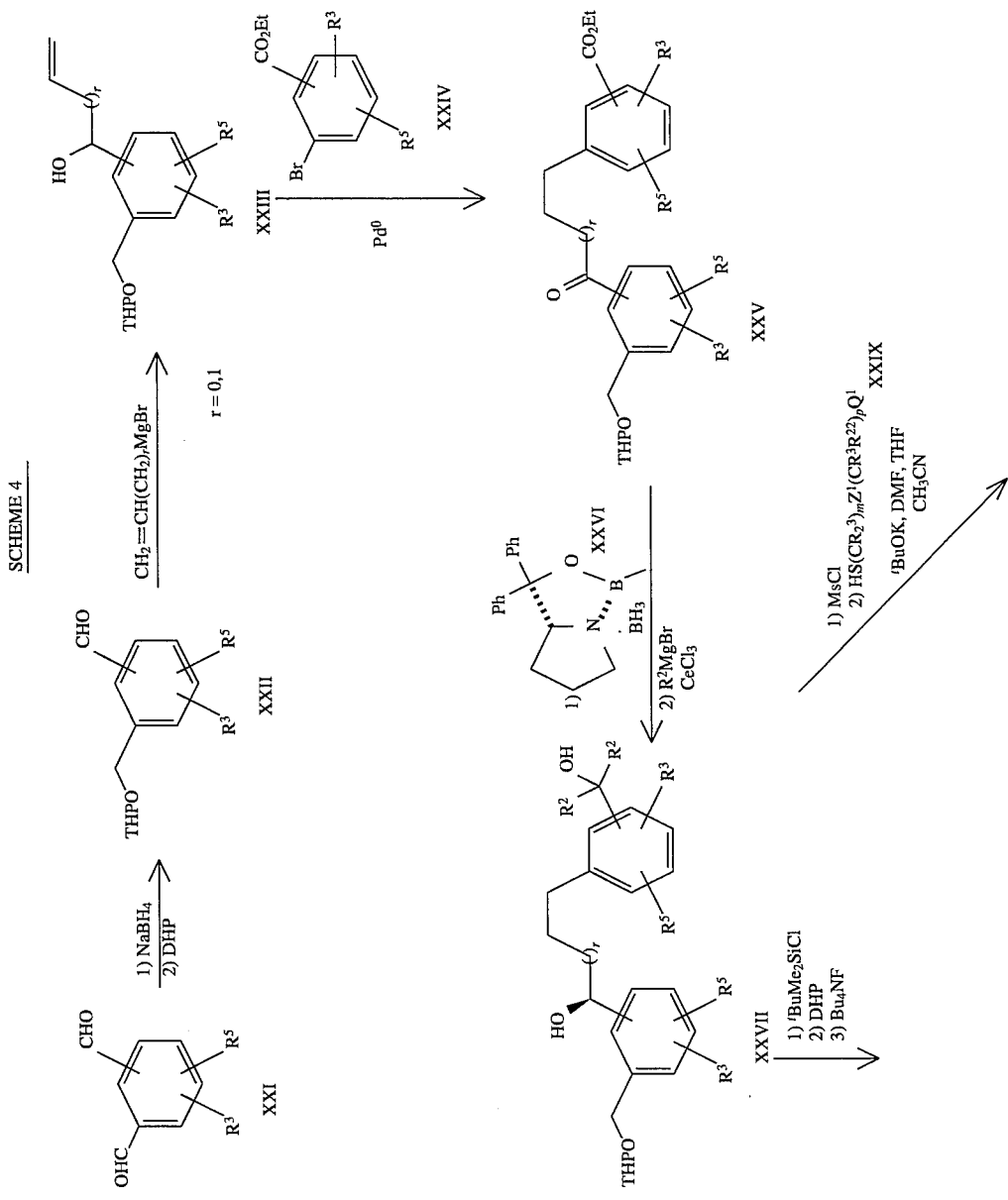

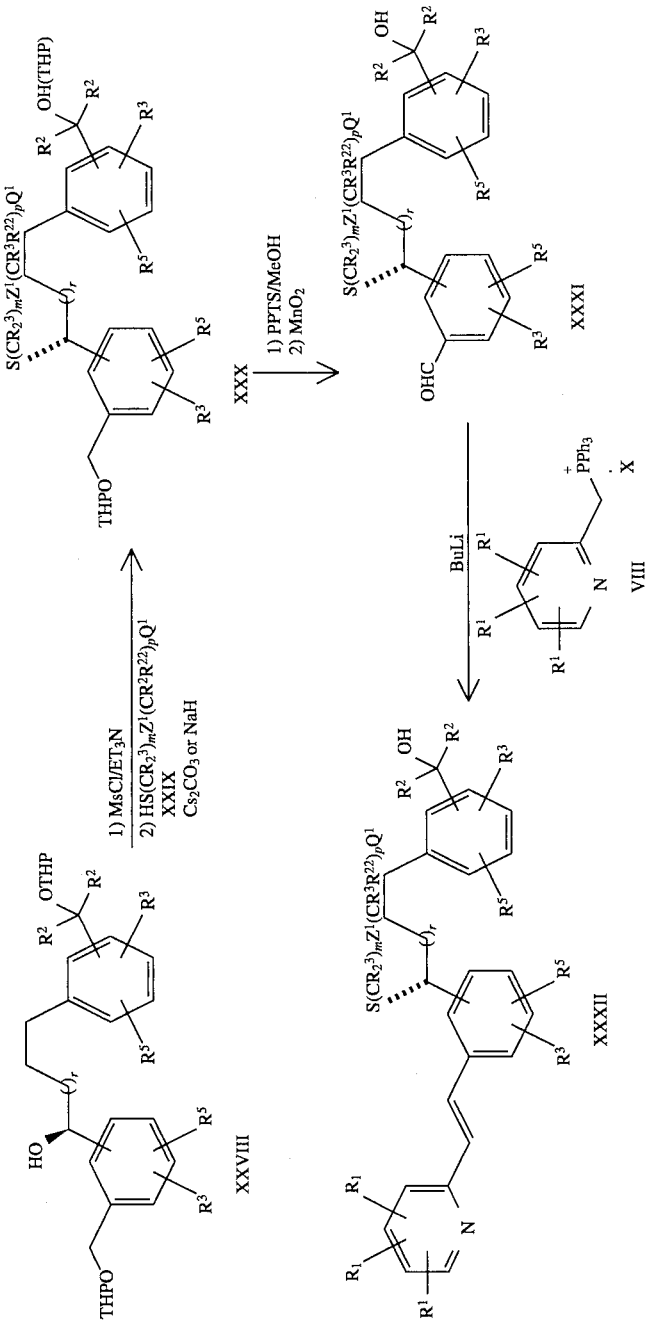

SCHEME 5
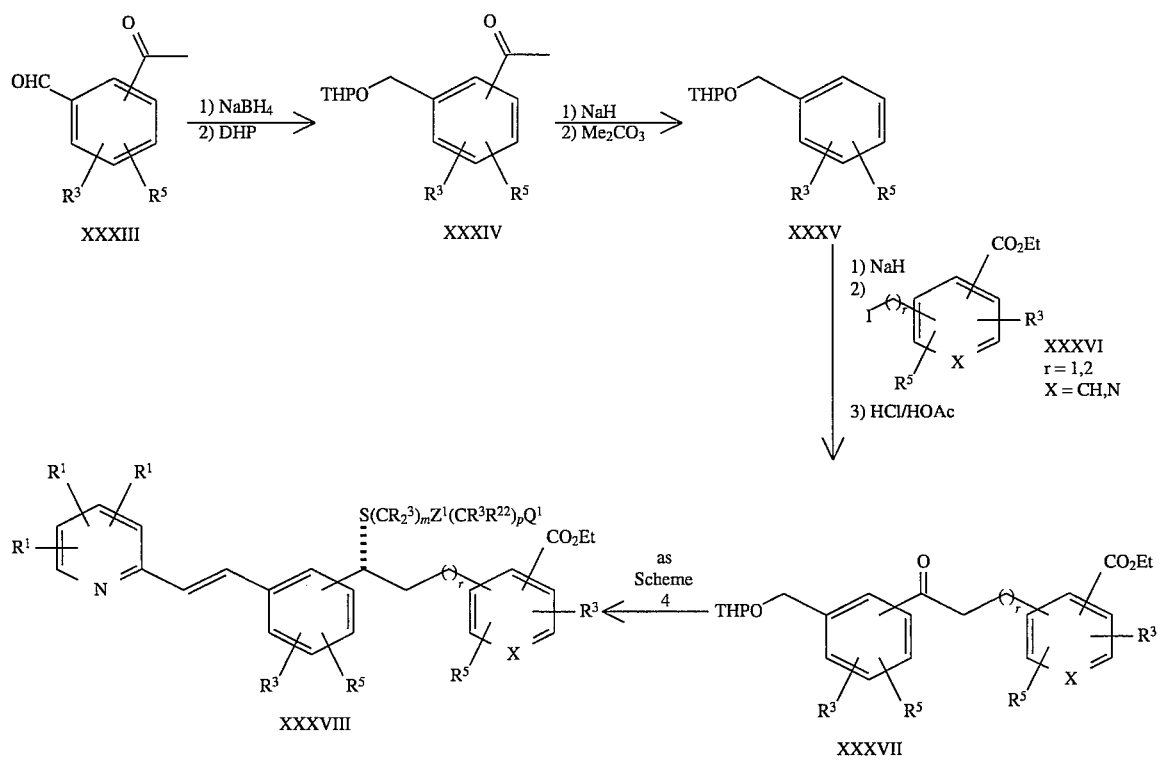
SCHEME 6
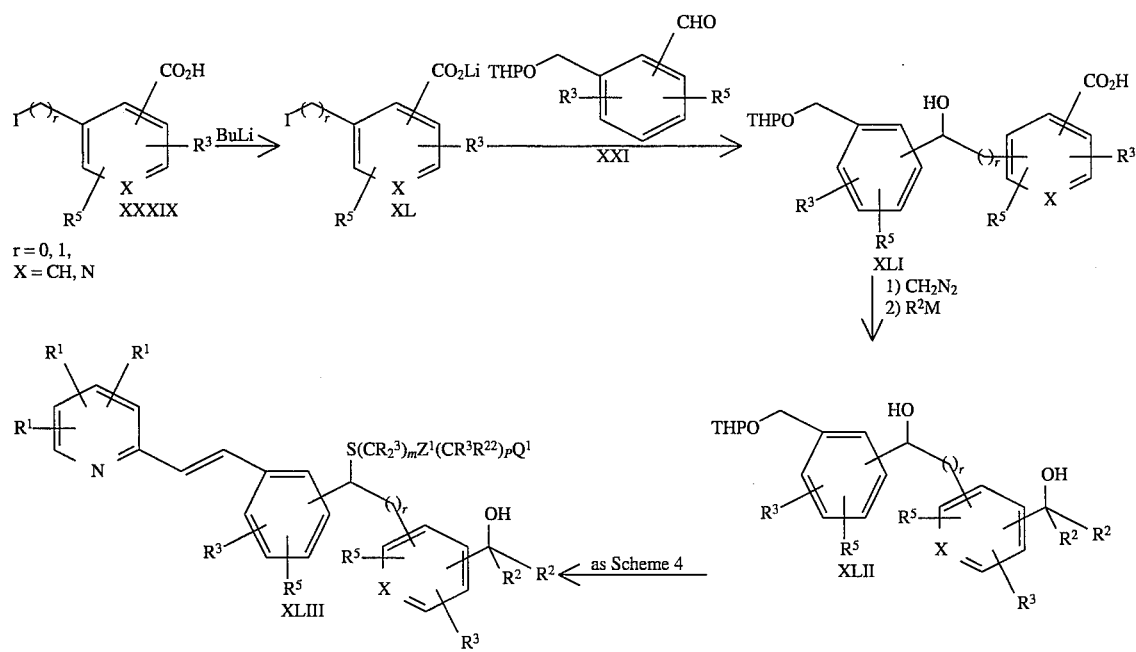

SCHEME 7
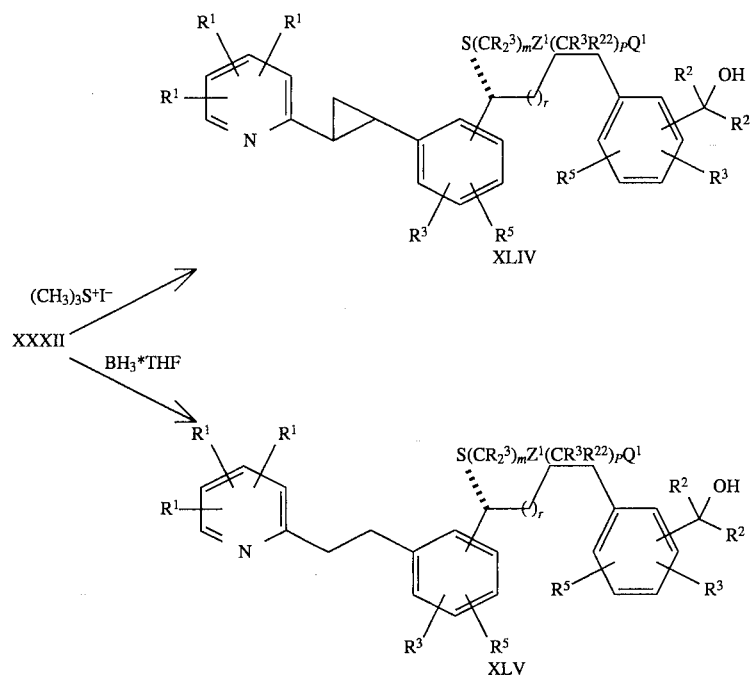
SCHEME 8
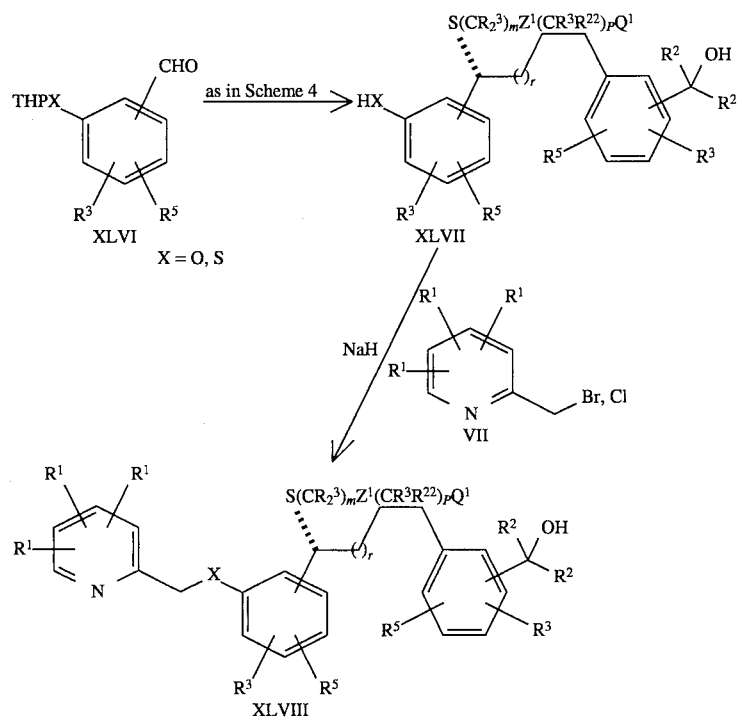

REPRESENTATIVE COMPOUNDS

Table I illustrates compounds of formula Ib, which are representative of the present invention.

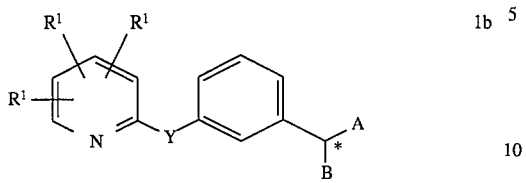

TABLE I

| EX. | * | $R^1$ | $R^1$ | Y | A | B |
|---|---|---|---|---|---|---|
| 1 | R | 5-Me | 6-Me | CH=CH | $(CH_2)_2(1,2)phe)C(Me)_2OH$ | $SCH_2C(CH_2)_2CH_2COOH$ |
| 2 | R | 5-CF$_3$ | H | CH=CH | $(CH_2)_2(1,2)phe)C(Me)_2OH$ | $SCH_2C(CH_2)_2CH_2COOH$ |
| 3 | R | 6-Cl | H | CH=CH | $(CH_2)_2(1,2)phe)C(Me)_2OH$ | $SCH_2C(CH_2)_2CH_2COOH$ |
| 4 | R | 5-n-Bu | H | CH=CH | $(CH_2)_2(1,2)phe)C(Me)_2OH$ | $SCH_2C(CH_2)_2CH_2COOH$ |
| 5 | R | 4-Me | 6-Me | CH=CH | $(CH_2)_2(1,2)phe)C(Me)_2OH$ | $SCH_2C(CH_2)_2CH_2COOH$ |
| 6 | R | H | H | CH=CH | $(CH_2)_2(1,2)phe)C(Me)_2OH$ | $SCH_2C(CH_2)_2CH_2COOH$ |
| 7 | R | 5-OMe | H | CH=CH | $(CH_2)_2(1,2)phe)C(Me)_2OH$ | $SCH_2C(CH_2)_2CH_2COOH$ |
| 8 | R |  | 5,6-(CH$_2$)4— | CH=CH | $(CH_2)_2(1,2)phe)C(Me)_2OH$ | $SCH_2C(CH_2)_2CH_2COOH$ |
| 9 | R |  | 5,6-(CH$_2$)$_3$— | CH=CH | $(CH_2)_2(1,2)phe)C(Me)_2OH$ | $SCH_2C(CH_2)_2CH_2COOH$ |
| 10 | R | 5-pH | H | CH=CH | $(CH_2)_2(1,2)phe)C(Me)_2OH$ | $SCH_2C(CH_2)_2CH_2COOH$ |
| 11 | R | 6-i-Pr | H | CH=CH | $(CH_2)_2(1,2)phe)C(Me)_2OH$ | $SCH_2C(CH_2)_2CH_2COOH$ |
| 12 | R | 5-Et | 6-Me | CH=CH | $(CH_2)_2(1,2)phe)C(Me)_2OH$ | $SCH_2C(CH_2)_2CH_2COOH$ |
| 13 | R | 6-n-Bu | H | CH=CH | $(CH_2)_2(1,2)phe)C(Me)_2OH$ | $SCH_2C(CH_2)_2CH_2COOH$ |
| 14 | R | 6-c-Pen | H | CH=CH | $(CH_2)_2(1,2)phe)C(Me)_2OH$ | $SCH_2C(CH_2)_2CH_2COOH$ |
| 15 | R | 5-CF$_3$ | 6-c-Bu | CH=CH | $(CH_2)_2(1,2)phe)C(Me)_2OH$ | $SCH_2C(CH_2)_2CH_2COOH$ |
| 16 | R | 5-F | 6-i-Bu | CH=CH | $(CH_2)_2(1,2)phe)C(Me)_2OH$ | $SCH_2C(CH_2)_2CH_2COOH$ |
| 17 | R | 6-(4-F-Ph) | H | CH=CH | $(CH_2)_2(1,2)phe)C(Me)_2OH$ | $SCH_2C(CH_2)_2CH_2COOH$ |
| 18 | R | 5-CF$_3$CH$_2$ | 6-c-Pr-CH$_2$ | CH=CH | $(CH_2)_2(1,2)phe)C(Me)_2OH$ | $SCH_2C(CH_2)_2CH_2COOH$ |
| 19 | R | 5-Cl | 6-Ac | CH=CH | $(CH_2)_2(1,2)phe)C(Me)_2OH$ | $SCH_2CH(CH_3)CH_2Tz$ |
| 20 | RS |  | 5,6-CH$_2$CH$_2$CH$_2$CHMe— | CH=CH | $(CH_2)_2(4-F-1,2-phe)C(Me)_2OH$ | $SCH_2CH(CH_3)CH_2Tz$ |
| 21 | R |  | 5,6-(CH$_2$)6- | CH$_2$O | $(CH_2)_2(4-Cl-1,2-phe)C(Me)_2OH$ | $SCH_2C(CH_2)_2CH_2COOH$ |
| 22 | RS | 6-(2-Thia) | H | CH$_2$CH$_2$ | $(CH_2)_2(3-CF_3-1,2-phe)CHMeOH$ | $SCH_2CHEtCH_2,COOH$ |
| 23 | S | 5-Et | 6-Et | CH$_2$S | $CH_2(2,3-Thio)C(CH_2)_2OH$ | $SCH_2CH_2CHEtCOOH$ |
| 24 | R | 6-(2-Fu) | H | CH=CH | $CH_2(2,3-fur)CEtOH$ | $SCH_2C(Me)_2CONHSO_2CF_3$ |
| 25 | S | 6-Th | H | CH$_2$O | $(CH_2)_2(1,2-phe)C(Me)_2OH$ | $SCH_2C(CH_2)_2CH_2CO_2H$ |
| 26 | R | 5-CF$_3$CH$_2$CH$_2$ | 6-EtO | CH=CH | $(CH_2)_2(4-Cl-1,2-phe)C(Me)_2OH$ | $OCH_2C(CH_3)_2CH_2CO_2H$ |
| 27 | RS | 5-i-Pr | 6-MeOCH$_2$ | CH=CH | $(CH_2)_2(4-Cl-1,2-phe)C(Me)_2OH$ | $OCH_2CH(CH_3)CH_2Tz$ |
| 28 | RS | 3-F | 6-c-PrSCH$_2$ | CH$_2$O | $(CH_2)_2(4-F-1,2-phe)C(Me)_2OH$ | $SCH_2CH(C_2H_5)CH_2CONME_2$ |
| 29 | S | 5-c-Pr | 6-Me | CH$_2$CH$_2$ | $CH_2(4-F-1,2-phe)CMePhOH$ | $SCH_2CH_2CO_2H$ |
| 30 | R |  | 5,6-(CH$_2$)4- | CH$_2$CH$_2$ | $(CH_2)_2(3-Cl-1,2-phe)CHMeOH$ | $SCH_2CH_2CONHS(O)_2Ph$ |
| 31 | R |  | 5,6-CH$_2$CH$_2$CH(Me)— | CH$_2$S | $(CH_2)_2(5-F-1,2-phe)CMeCF_3OH$ | $SCH_2CH_2CONHS(O)_2CH_3$ |
| 32 | RS | 5-MeOCH$_2$ | 6-EtSCH$_2$ | CH=CH | $(6-CF_3-1,2-phe)CHCF_3OH$ | $SCH_2CH_2CONHS(O)_2CF_3$ |
| 33 | R | 5-Me | 6-C$_3$H$_5$ | CH$_2$O | $(CH_2)_2(4-CF_3-1,2-phe)C(CF_3)_2OH$ | $SCH_2C(CH_2)_2CH_2CONHS(O)_2Ph$ |
| 34 | R | 5-i-C$_3$H$_5$ | 6-Me | CH=CH | $(CH_2)_2(4-F-1,3-phe)CMeEtOH$ | $SCH_2C(CH_3)_2CH_2CO_2H$ |
| 35 | RS | 6-(2-Py) | H | CH=CH | $(CH_2)_2(4-F-1,4-phe)C(CH_2)_2OH$ | $SCH_2CH(C_2H_5)Tz$ |
| 36 | S | 5-Cl | 6-CF$_3$CH$_2$CHMe | CH=CH | $(CH_2)_2(4-F-1,2-phe)C(CH_2)_3OH$ | $SCH_2C(CH_2)_2NHS(O)_2CF3$ |
| 37 | R | 4-F | 5,6-(CH$_2$)$_4$ | CH$_2$S | $(CH_2)_2(4-F-1,2-phe)C(CH_2)_4OH$ | $SCH_2C(CH_2)_3CH_2CO_2H$ |
| 38 | R | 3-MeO | 5-(CF$_3$)$_2$CHCH$_2$ | CH=CH | $(CH_2)_2(4-F-1,2-phe)C(CH_2)_5OH$ | $SCH_2C(CH_2)_4CH_2CO_2H$ |
| 39 | R | 5-F | 6-(2-Py) | CH$_2$CH$_2$ | $(CH_2)_2(2,5-fur)C(Me)_2OH$ | $SCH_2C(CH_2)_5CH_2CO_2H$ |
| 40 | RS | 6-(2-Ox) | H | CH=CH | $(CH_2)_2(1,2-phe)C(Me)_2OH$ | $SCH_2C(CH_3)_2CH_2CO_2H$ |

Assays For Determining Biological Activity

The leukotriene antagonist properties of the compounds of the present invention are evaluated using the following assays.

Three assays are described in T. R. Jones et al., Can. J. Physiol. Pharmacol., 1989, 67, 17–28. These are:

1) LTD$_4$ Receptor Binding Assays in Guinea Pig Lung Membranes,

2) Guinea Pig Trachea, and

3) In Vivo Assays in Anesthetized Guinea Pigs.

Asthamtic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mg/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

Pulmonary Mechanics In Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or *Ascaris suum* antigen.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., Prostaglandins, 28, 173–182 (1984) and McFarlane, C. S. et al., Agents Actions, 22, 63–68 (1987).)

Prevention Of Induced Bronchoconstriction In Allergic Sheep

A. Rationale:

Certain alergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods:

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.) and b) they have previously responded to inhalation challenge with *Ascaris suum* with both an acute bronchoconstriction and a late bronchial obstruction (W. M. Abraham et al., Am. Rev. Resp. Dis., 128, 839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one ml of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascaris suum* extract (1:20) are generated using a disposable medicalnebulizer (Raindrop®, Puritan Bennett), which produces an aerosol with a mass median aerodynamic diameter of 6.2 μM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is conected to the inspiratory part of a Harvard respirator. The aerosol is delivered at a tidal volume of 500 mL of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5–1 hr prior to Ascaris challenge and for 8 hrs after Ascaris as described above.

Statistical Analysis: A Kruskal-Wallis one way ANOVA test is used to compare the acute immediate responses to antigen and the peak late response in the controls and the drug treated animals.

The invention is further defined by the following non-limiting examples in which, unless stated otherwise:

(i) all operations were carried out under a nitrogen atmosphere at room or ambient temperature, that is, at a temperature in the range 18°–25° C.;

(ii) evaporation of solvent was carried out using a rotary evaporator under reduced pressure (600–4000 pascals: 4.5–30 mm. Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) final products were essentially pure by TLC and had satisfactory nuclear magnetic resonance (NMR) spectra, microanalytical data, and/or mass spectra;

(vi) yields are given for illustration only and, for crystalline end-products, refer to the weight of recrystallized solid;

(vii) when given, NMR data are in the form of delta (δ) values for major diagnostic protons, given in parts per million (ppm) relative to tetramethylsilane (TMS) as internal standard, determined at 250 MHz or 300 MHz using the indicated solvent; conventional abbreviations for signal shape are used for example, s. singlet; d. doublet; m. multiplet; hr. broad); "Ar" signifies an aromatic signal;

(viii) chemical symbols have their usual meanings; the following abbreviations have also been used: v (volume), w (weight), b.p. (boiling point), m.p. (melting point), L (liter(s)), mL (milliliters), µL (microliters), g (gram(s)), mg (milligram(s)), mol (moles), mmol (millimoles), eq. (equivalent(s)), h (hour (s)).

EXAMPLE 1

(R)-Sodium 1-(((1-(3-(2-(5,6-dimethyl-2-pyridinyl) ethenyl)phenyl)-3-(2-(2-hydroxy-2-propyl)phenyl) propyl)thio)methyl)cyclopropaneacetate Step 1: 2,3-Dimethylpyridine N-oxide To the 2,3-dimethylpyridine (15.0 g, 140 mmol) in CHCl$_3$ (40 mL) at 0° C. was slowly added a CHCl$_3$ (200 mL) solution of m-chloroperbenzoic acid (21.5 g, 154 mmol). The mixture was stirred 1 hour at 0° C., the ice bath was removed and stirring continued another hour. Calcium hydroxide (26 g, 350 mmol) was added and the slurry was vigorously stirred 4.5 hours before filtering through celite. The cake was thoroughly washed with CH$_2$Cl$_2$. Evaporation of the solvents left an oily solid that was swished in Et$_2$O giving 8.71 g of desired product which was used without further purification.

Step 2: 5,6-Dimethyl-2-pyridinecarbonitrile

To a slurry of N-oxide from Step 1 (8.7 g) in CH$_2$Cl$_2$ (125 mL) at r.t. was added trimethylsilylcyanide (9.9 mL, 74.2 mmol). After stirring for 15 minutes, N,N-diethylcarbamoyl chloride (9.4 mL, 74.2 mmol) was added and the resulting mixture was allowed to stir at r.t. for 2.5 days. The reaction was quenched by careful addition of 10% aq. K$_2$CO$_3$, stirred 15 minutes, and extracted (3×) with CH$_2$Cl$_2$. The organic layer was washed with aq. K$_2$CO$_3$, brine, and dried over Na$_2$SO$_4$/K$_2$CO$_3$. Evaporation of the solvent and purification of the residue by flash chromatography (25% to 50% Et$_2$O in hexanes) yielded 4.13 g of the title compound.

$^1$H NMR (CD$_3$COCD$_3$): δ 7.73 (1H, d), 7.62 (1H, d), 2.51 (3H, s), 2.39 (3H, s).

Step 3: Methyl-5,6-dimethyl-2-pyridinecarboxylate

Dry HCl (gas) was bubbled through anhydrous MeOH (125 mL) at −10° C. until saturation. The cyanopyridine from Step 2 (1.33 g, 10 mmol) was added and HCl was bubbled for another 5 minutes. The flask was sealed and the reaction allowed to stir 3 days at r.t. After carefully depressurizing the flask, water (3 mL) was added before concentrating in vacuo. The residue was diluted with EtOAc and saturated aq. NaHCO$_3$. Extraction of the aqueous phase with EtOAc (2×) followed by washing of the organic layers with aq. NaHCO$_3$, and brine gave upon concentration in vacuo 1.59 g (96%) of desired carbomethoxypyridine.

1H NMR (CD$_3$COCD$_3$): δ 7.8 (1H, d), 7.65 (1H, d), 3.85 (3H, s), 2.5 (3H, s), 2.35 (3H, s).

Step 4: 5,6-Dimethyl-2-(hydroxymethyl)pyridine

Diisobutyl aluminum hydride (4.45 mL, 25 mmol) was added to the carbomethoxypyridine from Step 3 (1.4 g, 8.4 mmol ) in THF (40 mL) at −78° C. The mixture was stirred overnight with slow warming to +4° C. The reaction was quenched with solid tartaric acid followed by aqueous sodium potassium tartrate and stirred ½ hour. Neutralization with saturated aq. NaHCO$_3$ and extraction with EtOAc (3×) gave after treatment with brine and evaporation 1.12 g (97%) of the title compound.

$^1$H NMR (CD$_3$COCD$_3$): δ 7.5 (1H, d), 7.15 (1H, d), 4.45 (2H, brs), 2.4 (3H, s), 2.22 (3H, s).

Step 5: 2-Bromomethyl-5,6-dimethylpyridine

Bromine (1M/CCl$_4$, 3.6 mL, 3.6 mmol) was added to a −5° C. solution of triphenylphosphine (943 mg, 3.6 mmol) in CH$_2$Cl$_2$ (12 mL). The color faded away and a solid precipitated. The mixture was warmed to r.t. and the pyridinecarbinol from Step 4 (411 mg, 3.0 mmol) was added dropwise as a CH$_2$Cl$_2$ (5 mL) solution. After stirring 1 hour, the reaction mixture was quenched with saturated aq. NaHCO$_3$, extracted with EtOAc (3×) and the combined organic extracts were washed with brine and dried over Na$_2$SO$_4$. Evaporation of the solvents left a crude residue (1.8 g) which was purified on a short silica gel column (20% EtOAc in hexanes) to give 546 mg (91%) of crystals of the title compound.

$^1$H NMR (CD$_3$COCD$_3$): δ 7.5 (1H, d), 7.25 (1H, d), 4.45 (2H, s), 2.42 (3H, s), 2.27 (3H, s).

Step 6: ((5,6-Dimethyl-2-pyridinyl)methyl)triphenylphosphonium bromide

The bromide from Step 5 (740 mg, 3.7 mmol) and triphenylphosphine (1.31 g, 5 mmol) were dissolved in acetonitrile (15 mL) and the mixture was refluxed for 6 hours. Evaporation of the solvent in vacuo left a solid that was swished in Et$_2$O. Filtration and vacuum drying of the powder gave 1.46 g (86%) of the desired phosphonium salt.

Step 7: 1,1-Cyclopropanedimethanol cyclic sulfite

To a solution of BH$_3$: THF complex (1M in THF, 262 mL) was added diethyl 1,1-cyclopropanedicarboxylate (25 g, 134 mmol) at 25° C. under N$_2$. The solution was heated at reflux for 6 hr, cooled to r.t., and MeOH (300 mL) was cautiously added. The solution was stirred for 1 hr and then concentrated to an oil. The crude diol was dissolved in CH₂Cl₂ (234 mL) and SOCl₂ (15.9 g, 134 mmol) was added dropwise over a period of 15 min at 25° C. After stirring for another 15 min, the mixture was washed with aqueous NaHCO₃. The organic extract was dried over Na₂SO₄, filtered and concentrated to give quantitatively the title compound as a white solid.

Step 8: 1-(Hydroxymethyl)cyclopropaneacetonitrile

To a solution of the cyclic sulfite product of step 7 (14.7 g, 99 mmol) in DMF (83 mL) was added NaCN (9.74 g, 199 mmol). The mixture was heated to 90° C. for 20 h. Upon cooling, EtOAc (400 mL) was added and the solution was washed with saturated NaHCO₃ solution (55 mL), H₂O (4×55mL), saturated NaCl solution and dried over Na₂SO₄. The solution was concentrated to give 7.1 g (65%) of the title compound.

Step 9: 1-(Acetythiomethyl)cyclopropaneacetonitrile

To a solution of the alcohol of Step 8 (42 g, 378 mmol) in dry CH₂Cl₂ (450 mL) at −30° C. was added Et₃N (103.7 mL, 741 mmol) followed by CH₃SO₂Cl (43.3 mL, 562 mmol) dropwise. The mixture was warmed to 25° C., washed with NaHCO₃, dried over Na₂SO₄ and concentrated in vacuo to give the corresponding mesylate. The mesylate was then dissolved in DMF (450 mL) and cooled to 0° C. Potassium thioacetate (55.4 g, 485 mmol) was added, and the mixture was stirred at 25° C. for 18 hr. EtOAc (1.5 L) was added, the solution was washed with NaHCO₃, dried over Na₂SO₄ and concentrated in vacuo to give 45 g (70%) of the title compound.

Step 10: Methyl 1-(thiomethyl)cyclopropaneacetate

To a solution of the nitrile of Step 9 (45 g, 266 mmol) in MeOH (1.36 L) was added H₂O (84 mL) and conc. H₂SO₄ (168 mL). The mixture was heated to reflux for 20 hr, cooled to 25° C., H₂O (1 L) was added and the product was extracted with CH₂Cl₂ (2×1.5 L). The organic extract was washed with H₂O and dried over Na₂SO₄. Concentration of the organic solution gave 36 g (93%) of the title compound.

Step 11: 3-((2-Tetrahydropyranyl)oxymethyl) benzaldehyde

Isophthalaldehyde (150 g, 1.1 mole ) was dissolved in THF (1 L) and EtOH (1 L) at 0° C. Sodium borohydride (11.0 g, 291 mmol) was added portionwise and the mixture stirred 1 hour at 0° C. Addition of 25% aq. NH₄OAc and extraction with EtOAc (2×) gave after evaporation the crude product. Purification by flash chromatography (20% to 40% EtOAc in hexanes) yielded 60 g of m-hydroxymethylbenzaldehyde.

This alcohol (0.44 mole) was dissolved in CH₂Cl₂ (500 mL), dihydropyran (50 g, 0.59 mole) and p-toluenesulfonic acid (1 g, 5 mmol) were added and the mixture was stirred overnight at r.t. After concentration in vacuo, the residue was purified by flash chromatography (5% to 15% EtOAc in toluene) to give 85 g of the title compound.

Step 12: 3-((2-Tetrahydropyranyl)oxymethyl)-2-propene-1-ol

To the aldehyde of Step 11 (85 g, 386 mmol) in toluene (1 L) at 0° C. was slowly added vinyl magnesium bromide (450 mL, 1M, 450 mmol) over a 30 minute period. After stirring for 1 hour the reaction mixture was quenched with 25% aq. NH₄OAc and extracted with EtOAc (3×). Evaporation and purification by flash chromatography (15% to 25% EtOAc in toluene) yielded 82 g (86%) of the title compound.

Step 13: Ethyl 2-(3-(3-((2-tetrahydropyranyl)oxymethyl)phenyl)-3-oxopropyl)benzoate The allylic alcohol of Step 12 (24.8 g, 100 mmol ) and ethyl o-bromobenzoate (25.2 g, 110 mmol ) were dissolved in DMF (200 mL). Lithium chloride (4.2 g, 100 mmol), lithium acetate dihydrate (25.5 g, 250 mmol), and tetra-n-butylammonium chloride (55 g, 200 mmol) were added and the resulting mixture was degassed three times. Palladium (II) acetate (1 g) was then added and the mixture was degassed three more times before heating it at 100° C. while stirring for 1 hour. After cooling to r.t., the reaction mixture was poured onto H₂O (600 mL), 10% aq. NaHCO₃ (200 mL) and Et₂O. The crude product was extracted with Et₂O (2×), washed with H₂O and brine, and dried over Na₂SO₄ before concentrating in vacuo. Purification on a short silica gel column (20% EtOAc in hexanes) gave 34 g (86%) of the title compound.

¹H NMR (CD₃COCD₃): δ 8.02 (1H, brs), 7.92 (1H, d), 7.88 (1H, d), 7.62 (1H, d), 7.50 (3H, m), 7.32 (1H, brt), 4.8 (1H, d), 4.70 (1H, brs), 4.54 (1H, d), 4.3 (2H, q), 3.82 (1H, m), 3.50 (1H, m), 3.35 (4H, m), 1.9–1.45 (6H, m), 1.32 (3H, t).

Step 14: Ethyl 2-(3-(3-((2-tetrahydropyranyl)oxymethyl)phenyl)-3(S)-hydroxypropyl)benzoate The keto ester of Step 13 (24.8 g, 62.5 mmol) was dissolved in THF (230 mL) and cooled to −45° C. A THF (15 mL) solution of tetrahydro-1-methyl-3,3-diphenyl-1H,3H-pyrrolo[1,2-c][1,3,2]oxazaborole-borane adduct (J. Org. Chem., 56, 751 (1991), 4.55 g, 15.6 mmol) was added dropwise and the resulting mixture was stirred 20 minutes at −45° C. To this solution, 1.0M borane-THF (62.5 mL, 62.5 mmol) was added dropwise over 30 minutes. The reaction mixture was stirred 1 hour at −45° C. followed by another 2 hours with slow warming to −20° C. After cooling the solution of −40° C., it was poured onto 25% aq. NH₄OAC (425 mL) and 1.0M diethanolamine (40 mL) at 0° C. and stirred vigorously for 20 minutes. The title compound was extracted with EtOAc (3×), dried over MgSO₄ and concentrated under reduced pressure. The crude oil was purified by flash chromatography (25% to 50% EtOAc in hexanes) to yield 22.6 g (91%) of the desired product as an oil.

$[\alpha]_D^{25}=-32.6°$ (C=3, CHCl₃)

Step 15: 2-(3-(3-((2-Tetrahydropyranyl)oxymethyl) phenyl)-3(S)-hydroxypropyl)-α,α-dimethylbenzenemethanol Anhydrous CeCl₃ (17.25 g, 70 mmol) was refluxed for 2.5 hours in THF (200 mL) using a Dean-Stark trap filled with molecular sieves to remove H₂O. The ivory suspension was cooled to −5° C. and MeMgCl (114 mL, 3M/THF, 340 mmol) was added dropwise while keeping the internal temperature between −10° C. and 0° C. The grey suspension was stirred 2 hours before slowly adding to it the hydroxy-ester of Step 14 (27.,1 g, 68 mmol) as a THF solution (200 mL) via a cannula. The resulting mixture was stirred 1.5 hours at or below 0° C., and then slowly poured onto ice cold 1M AcOH (1 L) and EtOAc (500 mL) and stirred for 30 minutes. After adjusting the pH to 6–7, the crude compound was extracted with EtOAc (2×) and the combined organic phases were washed with saturated aq. NaHCO₃ followed with brine. Purification on a short silica gel column (30% to 50% EtOAc in hexanes) yielded 24.5 g (95%) of the title compound.

Step 16: Methyl 1-(((3-(2-(2-hydroxy-2-propyl)phenyl)-1(R)-(3-((2-tetrahydropyranyl)oxymethyl)phenyl)propyl)thio)methyl)cyclopropaneacetate The diol of Step 15 (17.9 g, 46.6 mmol) was dissolved in CH₃CN (40 mL) and DMF (10 mL) and cooled to −42° C. under nitrogen. Diisopropylethylamine (8.5 mL, 48.9 mmol) was added followed by methanesulphonyl chloride (3.6 mL, 46.6 mmol) dropwise. The solution was stirred 1.5 hours with a mechanical stirrer while maintaining the temperature between −42° C. and −35° C.; then it was cooled to −45° C. The thiol of Step 10 (7.84 g, 48.9 mmol) was added followed by dropwise addition of DMF (15 mL). The potassium tert-butoxide in THF solution (56 mL, 1.75M, 97.9 mmol) was added to the reaction mixture within 20 minutes using a syringe pump. Stirring continued for 5 hours with slow warming from −35° C. to −22° C., giving a very thick translucid gel. The reaction was quenched with saturated aq. NH$_4$Cl (250 mL) and EtOAc (300 mL). The product was extracted with EtOAc, washed with H$_2$O and brine, and dried over MgSO$_4$. Purification by flash chromatography (20% to 30% EtOAc in hexanes) gave 16.8 g (68%) of the title compound.

Step 17: (R)Methyl 1-(((1-(3-(hydroxymethyl)phenyl)-3-(2-(2-hydroxy-2 -propyl)phenyl)propyl)thio)methyl)cyclopropaneacetate To the hydroxy ester from Step 16 (9.02 g, 17.1 mmol) in anhydrous methanol (60 mL) under nitrogen was added pyridine (50 µL) followed by pyridinium p-toluenesulfonate (1.1 g, 4.3 mmol). The reaction mixture was stirred 3.5 hours at 55° C., then at r.t. overnight before concentrating in vacuo. The residue was diluted with EtOAc (500 mL) and washed with H$_2$O, saturated aq. NaHCO$_3$, NaH$_2$PO$_4$ buffer (pH=4.5) and with brine. After drying over MgSO$_4$ and evaporation of the solvents, the product was purified by flash chromatography (40% to 60% EtOAc in hexanes) giving 6.85 g (91%) of the title compound.

$^1$H NMR (CD$_3$COCD$_3$): δ 7.41 (2H, m), 7.27 (3H, m), 7.09 (3H, m), 4.63 (2H, d), 4.19 (1H, t), 3.95 (1H, t), 3.88 (1H, s), 3.57 (3H, s), 3.1 (1H, ddd), 2.8 (1H, ddd), 2.5 (2H, s), 2.4 (2H, d), 2.17 (2H, m), 1.52 (6H, s), 0.52–0.35 (4H, m).

Step 18: (R) Methyl 1-(((1-(3-formylphenyl)-3-(2-(2 -hydroxy-2-propyl)phenyl)propyl)thio)methyl) cyclopropaneacetate To the dihydroxy-ester from Step 17 (6.8 g, 5.4 mmol) in EtOAc (150 mL) at 50° C. was added manganese dioxide (6.7 g, 76.8 mmol). After stirring for 30 minutes at 50° C. more MnO$_2$ (6.7 g) was added, and 30 minutes later, a third portion of MnO$_2$ (6.7 g) was added. An hour later, the warm reaction mixture was filtered through celite and the cake was washed with additional EtOAc. Evaporation of the solvents gave 5.62 g (83%) of the desired aldehyde.

$^1$H NMR (CD$_3$COCD$_3$): δ 10.4 (1H, s), 7.9 (1H, brs), 7.8 (2H, m), 7.58 (1H, t), 7.38 (1H, brd), 7.1 (3H, m), 4.1 (1H, t), 3.54 (3H, s), 3.13 (1H, ddd), 2.85 (1H, ddd), 2.51 (2H, s), 2.49 (2H, d), 2.2 (2H, m), 1.51 (6H, s), 0.52–0.32 (4H, m).

Step 19: (R)-Methyl 1-(((1-(3-(2-(5,6-dimethyl-2 -pyridinyl)ethenyl)phenyl)-3-(2-(2-hydroxy-2-propyl)phenyl)propyl)thio)methyl)cyclopropanacetate To a suspension of the phosphonium salt from Step 6 (924 mg, 2.0 mmol) in dry THF (10 mL) at −78° C. was added n-BuLi (800 µL, 2.5M in hexanes, 2 mmol). The orange mixture was stirred 30 min. at −78° C., warmed to −0° C. for 15 min. and then cooled to −78° C. The aldehyde from Step 18 (2 mL, 0.5M/THF, 1 mmol) was added and the resulting mixture was allowed to stir for 2 hours with slow warming to r.t. Saturated aq. NH$_4$Cl was added and the mixture extracted with EtOAc (2×). The organic extracts were washed with brine, dried over Na$_2$SO$_4$ and concentrated to an oil. Purification of the crude oil by flash chromatography (30% EtOAc in hexanes) gave 423 mg (78%) of the title compound.

$^1$H NMR (CD$_3$COCD$_3$): δ 7.65–7.0 (12H, m), 4.0 (1H, t), 3.85 (1H, s), 3.53 (3H, s), 3.12 (1H, ddd), 2.85 (1H, ddd), 2.51 (2H, s), 2.45 (3H, s), 2.40 (2H, dd), 2.26 (3H, s), 2.20 (2H, m), 1.50 (6H, s), 0.52–0.35 (4H, m).

Step 20: (R)-Sodium 1-(((1-(3-(2-(5,6-dimethyl-2 -pyridinyl)ethenyl)phenyl)-3-(2- (2-hydroxy-2-propyl)phenyl)propyl)thio)methyl)cyclopropaneacetate To a solution of ester from Step 19 (423 mg, 0.78 mmol) in MeOH (50 mL) and THF (10 mL) was added aqueous 2N NaOH (800 µL, 1.6 mmol). The mixture was stirred overnight at r.t. Saturated aq. NH$_4$Cl was added and the mixture extracted with EtOAc (3×). The combined organic layers were washed with brine, dried over Na$_2$SO$_4$ and concentrated to an oil. Purification of this crude by flash chromatography (50% EtOAc in hexanes, then 1% AcOH in 70% EtOAc in hexanes) gave 382 mg (89%) of the corresponding acid. To this acid in EtOH (4 mL) and THF (1 mL) was added 2N NaOH (350 µL, 0.7 mmol). The solvents were evaporated and the product was lyophilysed to give the title compound.

acid $^1$H NMR (CD$_3$COCD$_3$): δ 7.7–7.0 (12H, m), 4.05 (1H, t), 3.12 (1H, ddd), 2.87 (1H, ddd), 2.57 (2H, s), 2.48 (3H, s), 2.43 (1H, brs), 2.29 (3H, s), 2.20 (2H, m), 1.52 (6H, s), 0.55–0.35 (4H, m).

sodium salt $^1$H NMR (CD$_3$SOCD$_3$): δ 8.1–7.45 (12H, m), 4.97 (1H, s), 4.40 (1H, t), 3.5 (1H, ddd), 3.15 (1H, ddd), 3.1–2.9 (2H, m), 2.9 (3H, s), 2.7 (3H, s), 2.7–2.4 (4H, m), 1.90 (3H, s), 1.88 (3H, s), 0.82 (2H, m), 0.65 (2H, m).

Analysis calculated for C$_{33}$H$_{38}$NO$_3$SNa·H$_2$O: C, 69.57; H, 7.08; N, 2.46

Found: C, 69.10; H, 7.16; N, 2.47

Mass spec. (FAB): [M+23]$^+$ at 574.4 (100%), MH+ at 552.3 (21%)

EXAMPLE 2

(R)-Sodium 1-(((1-(3-(2-(5-trifluoromethyl-2-pyridinyl)ethenyl) phenyl) -3-(2-(2-hydroxy-2-propyl)phenyl)propyl) thio)methyl)cyclopropaneacetate Step 1: 2-Methyl-5-(trifluoromethyl)pyridine To a slurry of polymer supported tetrakis-triphenylphosphine palladium (4.0 g, catalytic) in dioxane (40 mL) at r.t. was added 2-chloro-5-trifluoromethylpyridine (14.7 g, 81 mmol) followed by trimethylaluminum (32.5 mL, 2M in hexanes, 65 mmol). The mixture was stirred 6 hours at r.t., then heated to reflux overnight. After cooling to −25° C., the mixture was slowly poured onto (500 g) ice, stirred 10 min. and then tartaric acid (5 g) and sodium potassium tartrate (25 g) were added. Stirring was continued for 25 min. before filtering off solids. The filtrate was extracted with CH$_2$Cl$_2$ (4×200 mL) and the solvents were evaporated. Distillation of the residue under vacuum (20 mm Hg) afforded 4.2 g of a liquid. $^1$H NMR showed it to be a 1:5 mixture of dioxane and the title compound. This mixture was used without further purification.

Step 2: 2-Methyl-5(trifluoromethyl)pyridine N-oxide

To a solution of crude 2-methyl-5-trifluoromethylpyridine from Step 1 (3.8 g) in CHCl$_3$ (40 mL) was added m-chloroperbenzoic acid (3.0 g, 17.4 mmol) and the resulting mixture was stirred 5 hours at r.t. More peracid (1.5 g, 8.7 mmol) was added and the reaction stirred another 2 hours. Calcium hydroxide (3.0 g, 40.5 mmol) was added and the slurry was vigorously stirred 20 minutes before filtering through celite. Evaporation of the solvents gave 4.5 g of the title compound containing a little dioxane and CHCl$_3$. This material was used without further purification.

$^1$H NMR (CD$_3$COCD$_3$): δ 8.53 (1H, brs), 7.68 (1H, d), 7.52 (1H, d), 2.42 (3H, s).

Step 3: ((5-Trifluoromethyl)-2-pyridinyl)methyl)triphenylphosphonium chloride

To a solution of the pyridine N-oxide from Step 2 (4.5 g crude) in $CH_2Cl_2$ (30 mL) was added phosphoryl chloride (230 μL, 2.5 mmol) at r.t. Then triethylamine (3.5 mL, 25 mmol) and phosphoryl chloride (2.10 mL, 22.5 mmol) were added simultaneously at such a rate in order to cause the solution to reflux. After the addition, the mixture was heated to reflux for 1.5 hours, then stirred at r.t. overnight. Saturated aq. $NaHCO_3$ (75 mL), 25% aq. $NH_4OAc$ (50 mL) and $CH_2Cl_2$ (75 mL) were added and the resulting mixture was vigorously stirred for 15 minutes. The crude was obtained after extraction with $CH_2Cl_2$ (2×), drying over $MgSO_4$ and evaporation of the solvents. Purification by flash chromatography ($CH_2Cl_2$) gave after partial o evaporation of the solvent a $CH_2Cl_2$ solution of the desired 2-chloromethyl-5-trifluoromethylpyridine. To this was added triphenylphosphine (6.5 g, 25 mmol) and acetonitrile (10 mL). The mixture was heated to reflux for 2 hours ($CH_2Cl_2$ distills off), stirred at r.t. overnight and concentrated by distillation. Evaporation to dryness left a solid that was swished in $Et_2O$ (2×) affording 3.0 g of the title compound.

$^1$H NMR ($CDCl_3$): δ 8.5 (1H, brs), 8.32 (1H, d), 7.92–7.55 (16H, m), 6.02 (2H, d).

Step 4: (R)-Sodium 1-(((1-(3-(2-(5-trifluoromethyl -2-pyridinyl)ethenyl)phenyl)-3-(2-(2-hydroxy -2-propyl)phenyl)propyl)thio)methyl)cyclopropaneacetate Using the procedure described in Steps 7–20 of Example 1, the phosphonium salt of Step 3 was converted to the title compound.

Analysis calculated for $C_{32}H_{33}NO_3SF_3Na \cdot H_2O$: C, 63.04; H, 5.79; N, 2,30

Found: C, 60.50; H, 5.76; N, 2.11.

Mass spec. (FAB): 592 $[M+23]^+$ at 614 (100%), $MH^+$ at (57%)

$^1$H NMR ($CD_3COCD_3$): δ 8.88 (1H, s), 8.07 (1H, brd), 7.88 (1H, d), 7.73 (2H, m), 7.55–7.3 (5H, m), 7.05 (3H, m), 4.07 (1H, t), 3.3–2.6 (5H, m), 2.4–2.05 (4H, m), 1.56 (3H, s), 1.51 (3H, s), 0.45 (2H, m), 0.25 (2H, m).

EXAMPLES 3–5

Using the method described in Example 2 (Steps 2–4), starting from 6-chloro-2-picoline, 5-n-butyl-2-picoline and from 2,4,6-collidine, the compounds of Examples 3–5 were prepared.

Example 3: Exact mass found for $C_{31}H_{33}SO_3NClNa$ (M+I): 558.18465

Calculated: 558.1845635

Example 4: Mass spec. (FAB): $[M+23]^+$ at 602 (100%), $MH^+$ at 580 (32%)

Example 5: Mass spec. (FAB): $[M+23]^+$ at 574 (57%), $MH^+$ at 552 (20%)

EXAMPLE 6

Starting from 2-picolyl chloride and using the same method described in Example 1 (Steps 6–20), the compound of Example 6 was prepared.

Mass spec. (FAB): $[M+23]^+$ at 546 (33%), $MH^+$ at 524 (44%).

EXAMPLE 7

(R)-Sodium 1-(((1-(3-(2-(5-methoxy-2-pyridinyl)ethenyl)phenyl) -3-(2-(2-hydroxy-2-propyl)phenyl)propyl)thio)methyl) cyclopropaneacetate Step 1: 5-Methoxy-2-picoline Sodium hydride (3.6 g, 150 mmol) was added portionwise to 5-hydroxy-2-picoline (15.0 g, 137 mmol) in DMF (120 mL). After 30 min., $CH_3I$ (10.2 mL, 156 mmol) was added and the mixture stirred 2 hours at r.t. Water was added and the compound was extracted with $Et_2O$ (3×). The organic extracts were washed with brine (2×), dried over $Na_2SO_4$ and concentrated in vacuo to give 6.7 g of the title compound.

Step 2: 5-Methoxy-2-picoline N-oxide

The 5-methoxy-2-picoline from Step 1 (6.7 g) was treated with 30% $H_2O_2$ (6.12 mL) in acetic acid (40 mL) at 100° C. overnight. After cooling to r.t., excess $MnO_2$ was added and the slurry was stirred for 2 hours. Filtration and concentration in vacuo gave 7.0 g of the title N-oxide.

Step 3: (R)-Sodium 1-(((1-(3-(2-(5-methoxy-2 -pyridinyl)ethenyl)phenyl)-3-(2-(2-hydroxy -2-propyl)phenyl)propyl)thio)methyl)cyclopropaneacetate Using the same procedure described in Steps 3–4 of Example 2, the pyridine N-oxide of Step 2 was converted to the title compound. Exact mass found for $C_{32}H_{36}NO_4SNa(M+1)$: 554, 23414

Calculated: 554, 23410

EXAMPLE 8

(R)-Sodium 1-(((1-(3-(2-(5,6-cyclohexeno-2-pyridinyl)ethenyl) phenyl) -3-(2-(2-hydroxy-2-propyl)phenyl)propyl)thio) methyl)cyclopropaneacetate Step 1: 2-(Acetyoxymethyl)quinoline Sodium acetate (38.3 g, 467 mmol), $Cs_2CO_3$ (38.0 g, 116.7 mmol) and 2-chloromethylquinolinium hydrochloride (25.0 g, 116.7 mol) (Eur. Pat. Appl. 284174, 28 Sep. 1988) were mixed together in DMF (200 mL) and stirred overnight at 65° C. The reaction was quenched with saturated aq. $NH_4Cl$, the crude compound was extracted with EtOAc (3×), washed with brine and dried over $MgSO_4$. Concentration in vacuo and purification of the residue by flash chromatography (from 10% to 20% EtOAc in toluene) gave 22.11 g (94%) of the title compound.

$^1$H NMR ($CD_3COCD_3$): δ 8.32 (1H, d), 8.01 (1H, d), 7.95 (1H, d), 7.75 (1H, dr), 7.58 (2H, m), 5.33 (2H, s), 2.15 (3H, s).

Step 2: 6-Hydroxymethyl-2,3-cyclohexenopyridine

The 2-acetoxymethylquinoline from Step 1 (22.0 g, 109 mmol) was dissolved in TFA (100 mL) in a Parr pressure bottle. $PtO_2$ (1 g, 4.4 mmol) was added and the mixture was hydrogenated at 50 psi of hydrogen for 110 minutes. After concentrating overnight with a nitrogen stream and filtering off the catalyst, the residue was diluted with MeOH (100 mL) before addition of excess 10N NaOH (~20 mL). This solution was stirred 15 minutes, then quenched with solid $NH_4Cl$ and saturated aq. $NH_4Cl$ and extracted with EtOAc (3×). The organic layers were washed with brine, dried over $MgSO_4$ and concentrated to an oily solid. Purification by flash chromatography (from 30% to 50% acetone in CH$_2$Cl$_2$) gave a solid that was swished in Et$_2$O yielding 7.5 g (42%) of the title compound as an oily solid.

$^1$H NMR (CD$_3$COCD$_3$): δ 7.40 (1H, d), 7.15 (1H, d), 4.59 (2H, s), 4.40 (1H, brs), 2.80 (1H, t), 2.75 (2H, t), 1.9–1.7 (4H, m).

Step 3: ((5,6-Cyclohexeno-2-pyridinyl)methyl)triphenylphosphonium methanesulfonate Methanesulfonyl chloride (3.26 mL, 42.1 mmol) was added to a solution of hydroxymethylpyridine from Step 2 (5.5 g, 33.7 mmol) and triethylamine (6.1 mL, 43.8 mmol) in CH$_2$Cl$_2$ at −40° C. After stirring 2 hours with slow warming to −20° C., saturated aq. NaHCO$_3$ was added and the mixture was stirred 15 minutes before separation of the layers. The aqueous phase was extracted with EtOAc (2×) and the combined organic layers were washed with brine, dried over MgSO$_4$ and concentrated to give the corresponding crude mesylate (8.5 g). This oil was dissolved in acetonitrile (150 mL), triphenylphosphine (14.1 g, 53.9 mmol) was added and the solution was refluxed for 2 hours. Upon cooling and evaporation of the solvent, the solid residue was swished (2×) in Et$_2$O to give 16.5 g (97%) of the title compound.

$^1$H NMR (CDCl$_2$): δ 7.85–7.55 (15H, m), 7.50 (1H, d), 7.23 (1H, d), 5.32 (2H, d), 2.70 (3H, s), 2.62 (2H, m), 2.39 (2H, brt), 1.70 (4H, m).

Step 4: (R)-Sodium 1-(((1-(3-(2-(5,6-cyclohexeno -2-pyridinyl)ethenyl)phenyl)-3-(2-(2-hydroxy-2-propyl)phenyl)propyl)thio)methyl) cyclopropaneacetate Using the procedure described in Steps 7–20 of Example 1, the title compound was prepared from the phosphonium salt of Step 3.

Analysis calculated for C$_{35}$H$_{40}$NO$_3$SNa·1½H$_2$O: C, 69.51; H, 7.17; N, 2.32

Found: C, 69.17; H, 7.15; N, 2.11

Mass spec. (FAB): [M+23]$^+$ at 600 (26%), MH$^+$ at 578 (33%)

$^1$H NMR (CD$_3$COCD$_3$): δ 7.75–7.0 (12H, m), 4.02 (1H, brt), 3.25–2.6 (9H, m), 2.22 (2H, brs), 2.1 (2H, m), 1.8 (4H, m), 1.56 (3H, s), 1.51 (3H, s), 0.43 (2H, m), 0.25 (2H, m)

EXAMPLE 9

(R)-Sodium 1-(((1-(3-(2-(5,6-cyclopenteno-2-pyridinyl)ethenyl)phenyl)-3-(2-hydroxy-2-propyl)phenyl) propyl)thio)methyl)cyclopropaneacetate Step 1: 6-Methyl-2,3-cyclopentenopyridine Wet Raney Nickel (15 g) was heated at 135° C. in a mixture of dodecane (130 mL) and 1-octanol (70 mL, 440 mmol) for 30 minutes to remove most of the H$_2$O (Dean Stark trap). 2,3-cyclopentenopyridine (15.0 g, 126 mmol) was added and the resulting mixture was heated at 185° C. overnight. More Ra/Ni (5 g) and 1-octanol (15 mL, 94 mmol) were added and heating at 190° C. was continued for another 24 hours. After cooling to r.t., H$_2$O (150 mL) and hexanes (300 mL) were added; the aqueous phase was extracted with hexanes (3×), the combined organic layers were washed with 6N HCl (50 mL) followed by 1N HCl (40 mL). To this acid phase was added 10N NaOH until basic. Extraction with CH$_2$Cl$_2$ (3×), drying over MgSO$_4$ and evaporation of the solvents gave 15.2 g of the title compound containing ~10% of starting material.

$^1$H NMR (CDCl$_3$): δ 7.49 (1H, d), 6.90 (1H, d), 3.0 (2H, t), 2.9 (2H, t), 2.52 (3H, s), 2.12 (2H, m).

Step 2: (R)-Sodium 1-(((1-(3-(2-(5,6-cyclopenteno -2-pyridinyl)ethenyl)phenyl)-3-(2-hydroxy-2 -propyl)phenyl-)propyl)thio)methyl)cyclopropaneacetate Using the procedure described in Steps 2–4 of Example 2, the pyridine of Step 1 was converted into the title compound.

Analysis calculated for C$_{34}$H$_{38}$NO$_3$SNa·2H$_2$O: C, 68.09; H, 7.06; N, 2.34

Found: C, 65.71; H, 6.72; N, 2.01

Mass spec. (FAB): [M+23]$^+$ at 586 (20%), MH+ at 564 (31%)

$^1$H NMR (CD$_3$COCD$_3$): δ 7.7–7.0 (12H, m), 4.20 (1H, t), 3.2 (1H, ddd), 2.95–2.7 (9H, m), 2.6 (2H, dd), 2.3–2.0 (3H, m), 1.56 (3H, s), 1.51 (3H, s), 0.42 (2H, m), 0.23 (2H, m).

EXAMPLE 10

Starting from 3-phenylpyridine and using the same procedure as described in Example 9, the compound of Example 10 was prepared.

Mass spec. (FAB): [M+23]$^+$ at 622 (29%), MH$^+$ at 600 (13%).

EXAMPLE 11

(R)-Sodium 1-(((1-(3-(2-(6-isopropyl-2-pyridinyl)ethenyl)phenyl) -3-(2-(2-hydroxy-2-propyl)phenyl)propyl)thio) methyl)cyclopropaneacetate Step 1: 6-Ethyl-2-pyridinecarboxaldehyde To a solution of N,N,N-trimethylethylenediamine (4.29 mL, 33 mmol) in THF (20 mL) at −25° C. was added n-BuLi (13.2 mL, 2.5M in hexanes, 33 mmol). This solution was stirred 15 minutes, then transferred into a −78° C. solution of 6-methyl-2-pyridine-carboxaldehyde (3.63 g, 30 mmol) in THF (80 mL). After stirring 30 minutes at −78° C., a THF (50 mL) solution of lithium diisopropylamide (33 mmol) was added and the now dark red mixture was stirred 1 hour at −78° C. Methyl iodide (5.68 g, 40 mmol) in THF (10 mL) was added and reaction mixture was allowed to warm to r.t. for 4 hours. Water and 25% aq. NH$_4$OAc were added, the crude product was extracted with EtOAc (2×) and solvents were evaporated. Purification by flash chromatography (from 5% to 10% EtOAc in hexanes) gave 660 mg of the title compound.

Step 2: 6-Isopropyl-2-pyridinecarboxaldehyde

The alkylation of 6-ethyl-2-pyridinecarboxaldehyde from Step 1 was performed as described above for 6-methyl,2-pyridinecarboxaldehyde.

$^1$H NMR (CD$_3$COCD$_3$): δ 10.0 (1H, s), 7.93 (1H, t), 7.75 (1H, d), 7.57 (1H, d), 3.18 (1H, m), 1.32 (6H, d).

Step 3: 6-Isopropyl-2-(hydroxyethyl)pyridine

NaBH$_4$ (37 mg, 1 mmol) was added to a MeOH (400 μL) and THF (4 mL) solution of 6-isopropyl-2-pyridinecarboxaldehyde from Step 2 (160 mg, 1.07 mmol) at r.t. and the resulting mixture was stirred for 1 hour. Saturated aq. NH$_4$Cl was added and extraction with EtOAc (2×) gave, after evaporation of the solvents, 156 mg (97%) of the title compound which was used without further purification.

Step 4: (R)-Sodium 1-(((1-(3-(2-(6-isopropyl-2 -pyridinyl)ethenyl)phenyl)-3-(2-(2-hydroxy-2-propyl)phenyl)propyl)thio)methyl)cyclopropaneacetate Using the method described in Steps 5–20 of Example 1, the hydroxymethylpyridine of Step 3 was converted to the title compound.

Mass spec. (FaB): [M+23]$^+$ at 588 (100%), MH$^+$ at 566 (33%)

acid $^1$H NMR (CD$_3$COCD$_3$): δ 7.8–7.05 (13H, m), 4.05 (1H, t), 3.17 (1H, ddd), 3.07 (2H, m), 2.88 (1H, ddd), 2.6 (2H, s), 2.43 (2H, s), 2.2 (2H, m), 1.55 (6H, s), 1.30 (6H, d), 0.55–0.35 (4H, m).

EXAMPLE 12

(R)-Sodium
1-(((1-(3-(2-(5-ethyl-6-methyl-2-pyridinyl)
ethenyl)phenyl)-3-(2-(2-hydroxy-2-propyl)phenyl)
propyl)thio)methyl)cyclopropaneacetate Step 1: 5-Ethyl-6-methyl-2-pyridinecarbonitrile Potassium bis(trimethylsilyl)amide (41 mL, 0.5M in toluene, 20.4 mmol) was added to a solution of 2-cyano-5,6-dimethylpyridine from Example 1, Step 2 (2.45 g, 18.5 mmol) and hexamethylphosphoric triamide (9.7 mL, 55.6 mmol) in dry THF (30 mL) at −78° C. After stirring 30 minutes, MeI (5.77 mL, 92.7 mmol) was added and the reaction mixture stirred 45 minutes at −78° C. Saturated aq. $NH_4Cl$ was added, the mixture was extracted with EtOAc (3×), the organic layers were dried over $MgSO_4$ and concentrated in vacuo. The residue was purified by flash chromatography (from 15:15:70 to 20:20:60 of $Et_2O$: $CH_2Cl_2$: hexanes) to give 1.2 g (44%) of the title compound.

Step 2: Methyl 5-ethyl-6-methyl-2-pyridinecarboxylate

Dry HCl (gas) was bubbled through a MeOH (30 mL) solution of 2-cyanopyridine from Step 1 (1.4 g, 9.6 mmol) at 0° C. until saturation. The flask was sealed with a new rubber septum and the reaction mixture was stirred 30 hours at r.t. After careful depressurisation, $H_2O$ (5 mL) was added and the MeOH was evaporated. The aqueous residue was neutralized with saturated aq. $NaHCO_3$ and extracted with EtOAc (3×). The organic extracts were dried over $MgSO_4$, concentrated in vacuo, and the residue was purified by flash chromatography (from 30% to 50% EtOAc in hexanes) to give 1.49 g (87%) of the title compound.

$^1$H NMR ($CD_3COCD_3$): δ 7.85 (1H, d), 7.67 (1H, d), 3.86 (3H, s), 2.72 (2H, q), 2.52 (3H, s), 1.23 (3H, t).

Step 3: (R)-Sodium 1-(((1-(3-(2-(5-ethyl-6-methyl -2-pyridinyl)ethenyl)phenyl)-3-(2-(2-hydroxy-2-propyl)phenyl)propyl)thio)methyl)cyclopropaneacetate Using the procedure described in Steps 4–20 of Example 1, the methyl ester of Step 2 was converted to the title compound.

acid $^1$H NMR ($CD_3COCD_3$): δ 7.7–7.0 (12H, m), 4.05 (1H, t), 3.15 (1H, ddd), 2.75 (2H, m), 2.66 (2H, q), 2.58 (2H, s), 2.51 (3H, s), 2.43 (2H, d), 2.21 (2H, m), 1.52 (6H, s), 1.21 (3H, t), 0.55–0.4 (4H, m).

EXAMPLE 13

(R)-Sodium
1-(((1-(3-(2-(6-butyl-2-pyridinyl)ethenyl)phenyl)
-3-(2-(2-hydroxy-2-propyl)phenyl)propyl)thio)methyl)
cyclopropaneacetate Step 1: 6-(1-Butenyl)-2-picoline n-Butyllithium (7.5 mL, 1.6M/hexanes, 12 mmol) was added to a slurry of propyltriphenylphosphonium bromide (4.62 g, 12 mmol) in THF (40 mL) at −78° C. The mixture was warmed to 0° C. and stirred 30 min., then cooled again to −78° C. A THF (10 mL) solution of 6-methyl-2-pyridinecarboxaldehyde (1.21 g, 10 mmol) was added dropwise. The reaction mixture was allowed to warm to r.t. and stirred for 2 hours. Silica gel was added and the slurry was filtered on a short ($SiO_2$) column eluting with 10% EtOAc in hexanes to give 990 mg of the title compound.

Step 2: 6-Butyl-2-picoline

The picoline from Step 1 (970 mg) was hydrogenated for 50 minutes at 20 psi of hydrogen in EtOAc (30 mL) using 5% Pd/C (90 mg) as catalyst. Filtration and concentration in vacuo gave 910 mg of the title compound.

Step 3: (R)-Sodium 1-(((1-(3-(2-(6-butyl-2 -pyridinyl)ethenyl)phenyl)-3-(2-(2-hydroxy-2-propyl)phenyl)propyl)thio)methyl)cyclopropaneacetate Using the procedure described in Steps 2–4 of Example 2, the picoline of Step 2 was converted to the title compound.

Elemental Analysis calculated for $C_{35}H_{42}NO_3SNa·H_2O$: C, 70.32; H, 7.42; N, 2.34

Found: C, 70.34; H, 7.35; N, 1.86

Mass spec. (FAB): $[M+23]^+$ at 602 (80%), $MH^+$ at 580 (78%)

acid $^1$H NMR ($CD_3COCD_3$): δ 7.7–7.0 (13H, m), 4.05 (1H, t), 3.13 (1H, ddd), 2.88 (2H, m), 2.74 (2H, t), 2.56 (2H, s), 2.42 (2H, brs), 2.2 (2H, m), 1.72 (2H, m), 1.52 (6H, s), 1.40 (2H, m), 0.92 (3H, t), 0.55–0.35 (4H, m).

What is claimed is:

1. A compound of the Formula:

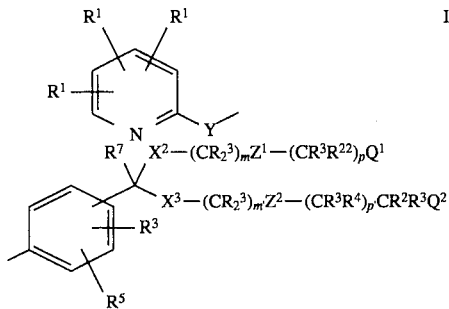

wherein:

$R^1$ is H, halogen, CN, lower alkyl, cycloalkyl, polyhalo lower alkyl, lower alkoxy, lower alkoxy lower alkyl, lower alkylthio lower alkyl, lower alkenyl, substituted or unsubstituted phenyl, or adjacent $R^1$'s and the carbons through which they are attached may form a saturated ring of 5 to 6 carbon atoms;

$R^2$ is lower alkyl, lower alkenyl, lower alkynyl, $-CF_3$, $-CH_2F$, $-CHF_2$, $-CH_2CF_3$, substituted or unsubstituted phenyl, substituted or unsubstituted benzyl, substituted or unsubstituted 2-phenethyl, or two $R^2$ groups joined to the same carbon may form a saturated ring of up to 8 members containing 0 heteroatom, or 1 to 2 heteroatoms chosen from O, S, and N and the resulting heterocycle is selected from the group consisting of tetrahydrofuran, tetrahydrothiophene, pyrrolidine, pyran, thiopyran, piperidine, dioxane, morpholine, thiomorpholine and piperazine;

$R^3$ is H or $R^2$;

$R^4$ is halogen, $-NO_2$, $-CN$, $-OR^3$, $-SR^3$, $NR^3R^3$, $NR^3C(O)R^7$, or $R^3$;

$R^5$ is H, halogen, $-NO_2$, $-N_3$, $-CN$, $-SR^2$, $-NR^3R^3$, $-OR^3$, lower alkyl, or $-C(O)R^3$;

$R^6$ is $-(CH_2)_s-C(R^7R^7)-(CH_2)_s-R^8$ or $-CH_2C(O)NR^{12}R^{12}$;

$R^7$ is H or lower alkyl;

$R^8$ is

A) 2,5-dioxo-1-pyrrolidinyl, (3-pyridinylcarbonyl)amino, 1,3-dihydro-1,3-dioxo-2H-isoindol-2-yl, 1,3-dihydro-2H-isoindol-2-yl, 2,4-imidazolinedion-1-yl, 2,6-piperidinedion-1-yl, 2-imidazolyl, 2-oxo-1, 3-dioxolen-4-yl, piperidin-1-yl, morpholin-1-yl, and piperazin-1-yl, or B) the radical W—R$^9$;

R$^9$ contains up to 20 carbon atoms and is (1) an alkyl group or (2) an alkylcarbonyl group of an organic acyclic or monocyclic carboxylic acid containing not more than 1 heteroatom in the ring;

R$^{10}$ is —SR$^{11}$, —OR$^{12}$, or —NR$^{12}$R$^{12}$;

R$^{11}$ is lower alkyl, —C(O)R$^{14}$, unsubstituted phenyl, or unsubstituted benzyl;

R$^{12}$ is H, R$^{11}$, or two R$^{12}$ groups joined to the same N may form a saturated 5 or 6-membered ring selected from the group consisting of pyrrolidine, piperidine, morpholine, thiamorpholine, piperazine, and N-methylpiperazine;

R$^{13}$ is lower alkyl, lower alkenyl, lower alkynyl, —CF$_3$, or substituted or unsubstituted phenyl, benzyl, or 2-phenethyl;

R$^{14}$ is H or R$^{13}$;

R$^{15}$ is R$^3$ or halogen;

R$^{16}$ is H, lower alkyl, or OH;

R$^{17}$ is lower alkyl, lower alkenyl, lower alkynyl, or substituted or unsubstituted phenyl, benzyl, or 2-phenethyl;

R$^{18}$ is lower alkyl, lower alkenyl, lower alkynyl, —CF$_3$, or substituted or unsubstituted phenyl, benzyl, or 2-phenethyl;

R$^{19}$ is lower alkyl, lower alkenyl, lower alkynyl, —CF$_3$, or substituted or unsubstituted phenyl, benzyl, or 2-phenethyl;

R$^{20}$ is H, lower alkyl, substituted or unsubstituted phenyl, benzyl, phenethyl, or pyridinyl, or two R$^{20}$ groups joined to the same N may form a saturated 5 or 6-membered ring selected from the group consisting of pyrrolidine, piperidine, morpholine, thiamorpholine, piperazine, and N-methylpiperazine;

R$^{21}$ is H or R$^{17}$;

R$^{22}$ is R$^4$, CHR$^7$OR$^3$, or CHR$^7$SR$^2$;

m and m' are independently 0–8;

p and p' are independently 0–8;

m+ p is 1–10 when X$^2$ is O, S, S(O), or S(O)$_2$;

m+p is 0–10 when X$^2$ is CR$^3$R$^{16}$ or a bond;

m'+ p' is 0–10;

s is 0–3;

Q$^1$ is —C(O)OR$^3$, 1H (or 2H)-tetrazol-5-yl, —C(O)OR$^6$, —C(O)NHS(O)$_2$R$^{13}$, —CN, —C(O)NR$^{12}$R$^{12}$, NR$^{21}$S(O)$_2$R$^{13}$, —NR$^{12}$C(O)NR$^{12}$R$^{12}$, —NR$^{21}$C(O)R$^{18}$, OC(O)NR$^{12}$R$^{12}$, —C(O)R$^{19}$, —S(O)R$^{18}$, —S(O)$_2$R$^{18}$, —S(O)$_2$NR$^{12}$R$^{12}$, —NO$_2$, NR$^{21}$C(O)OR$^{17}$, —C(NR$^{12}$R$^{12}$)=NR$^{12}$, or —C(R$^{13}$)=NOH; or if Q$^1$ is C(O)OH and R$^{22}$ is —OH, —SH, CHR$^7$OH or —NHR$^3$, then Q$^1$ and R$^{22}$ and the carbons through which they are attached may form a heterocyclic ring by loss of water;

Q$^2$ is OR$^3$;

W is O, S, or NR$^3$;

X$^1$ is O, S,—S(O)—, —S(O)$_2$—, —N(R$^3$)—, or —CR$^3$R$^3$—;

X$^2$ and X$^3$ are independently O, S, S(O), S(O)$_2$, CR$^3$R$^{16}$, or a bond;

Y is —CR$^3$=CR$^3$—, —C≡C—, —CR$^3$R$^3$—X$^1$, —X$^1$—CR$^3$R$^3$—;

Z$^1$ and Z$^2$ are independently a bond or

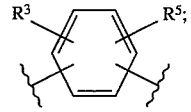

or a pharmaceutically acceptable salt thereof.

2. A compound of claim 1 of the Formula:

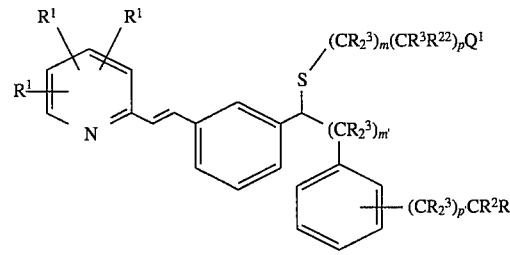

wherein:

R$^1$ is H, halogen, lower alkyl, polyhalo lower alkyl, lower alkoxy or adjacent R$^1$'s and the carbons through which they are attached may form a saturated ring of 5 to 7 carbon atoms;

R$^{22}$ is R$^3$, —CH$_2$OR$^3$, or —CH$_2$SR$^2$;

Q$^1$ is —C(O)OH, 1H(or 2H)-tetrazol-5-yl, —C(O)NHS(O)$_2$R$^{13}$, —C(O)NR$^{12}$R$^{12}$, or —NHS(O)$_2$R$^{13}$;

m' is 2 or 3;

p' is 0 or 1; and m+p is 1–5;

or a pharmaceutically acceptable salt thereof.

3. A compound of claim 1 of the Formula:

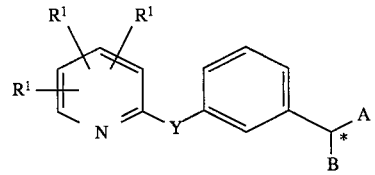

wherein the substituents are as follows:

| EX. | * | R$^1$ | R$^1$ | Y | A | B |
|---|---|---|---|---|---|---|
| 1 | R | 5-Me | 6-Me | CH=CH | (CH$_2$)$_2$(1,2)phe)C(Me)$_2$OH | SCH$_2$C(CH$_2$)$_2$CH$_2$COOH |
| 2 | R | 5-CF$_3$ | H | CH=CH | (CH$_2$)$_2$(1,2)phe)C(Me)$_2$OH | SCH$_2$C(CH$_2$)$_2$CH$_2$COOH |
| 3 | R | 6-Cl | H | CH=CH | (CH$_2$)$_2$(1,2)phe)C(Me)$_2$OH | SCH$_2$C(CH$_2$)$_2$CH$_2$COOH |
| 4 | R | 5-n-Bu | H | CH=CH | (CH$_2$)$_2$(1,2)phe)C(Me)$_2$OH | SCH$_2$C(CH$_2$)$_2$CH$_2$COOH |
| 5 | R | 4-Me | 6-Me | CH=CH | (CH$_2$)$_2$(1,2)phe)C(Me)$_2$OH | SCH$_2$C(CH$_2$)$_2$CH$_2$COOH |
| 6 | R | H | H | CH=CH | (CH$_2$)$_2$(1,2)phe)C(Me)$_2$OH | SCH$_2$C(CH$_2$)$_2$CH$_2$COOH |
| 7 | R | 5-OMe | H | CH=CH | (CH$_2$)$_2$(1,2)phe)C(Me)$_2$OH | SCH$_2$C(CH$_2$)$_2$CH$_2$COOH |

-continued

| EX. | * | R¹ | R¹ | Y | A | B |
|---|---|---|---|---|---|---|
| 8 | R | | 5,6-(CH$_2$)$_4$— | CH=CH | (CH$_2$)$_2$(1,2phe)C(Me)$_2$OH | SCH$_2$C(CH$_2$)$_2$CH$_2$COOH |
| 9 | R | | 5,6-(CH$_2$)$_3$— | CH=CH | (CH$_2$)$_2$(1,2phe)C(Me)$_2$OH | SCH$_2$C(CH$_2$)$_2$CH$_2$COOH |
| 10 | R | 5-pH | H | CH=CH | (CH$_2$)$_2$(1,2phe)C(Me)$_2$OH | SCH$_2$C(CH$_2$)$_2$CH$_2$COOH |
| 11 | R | 6-i-Pr | H | CH=CH | (CH$_2$)$_2$(1,2phe)C(Me)$_2$OH | SCH$_2$C(CH$_2$)$_2$CH$_2$COOH |
| 12 | R | 5-Et | 6-Me | CH=CH | (CH$_2$)$_2$(1,2phe)C(Me)$_2$OH | SCH$_2$C(CH$_2$)$_2$CH$_2$COOH |
| 13 | R | 6-n-Bu | H | CH=CH | (CH$_2$)$_2$(1,2phe)C(Me)$_2$OH | SCH$_2$C(CH$_2$)$_2$CH$_2$COOH |
| 14 | R | 6-c-Pen | H | CH=CH | (CH$_2$)$_2$(1,2phe)C(Me)$_2$OH | SCH$_2$C(CH$_2$)$_2$CH$_2$COOH |
| 15 | R | 5-CF$_3$ | 6-c-Bu | CH=CH | (CH$_2$)$_2$(1,2phe)C(Me)$_2$OH | SCH$_2$C(CH$_2$)$_2$CH$_2$COOH |
| 16 | R | 5-F | 6-i-Bu | CH=CH | (CH$_2$)$_2$(1,2phe)C(Me)$_2$OH | SCH$_2$C(CH$_2$)$_2$CH$_2$COOH |
| 17 | R | 6-(4-F-Ph) | H | CH=CH | (CH$_2$)$_2$(1,2phe)C(Me)$_2$OH | SCH$_2$C(CH$_2$)$_2$CH$_2$COOH |
| 18 | R | 5-CF$_3$CH$_2$ | 6-C-Pr-CH$_2$ | CH=CH | (CH$_2$)$_2$(1,2phe)C(Me)$_2$OH | SCH$_2$C(CH$_2$)$_2$CH$_2$COOH |
| 19 | R | 5-Cl | 6-Ac | CH=CH | (CH$_2$)$_2$(1,2phe)C(Me)$_2$OH | SCH$_2$CH(CH$_3$)CH$_2$Tz |
| 20 | RS | | 5,6-CH$_2$CH$_2$CH$_2$CHMe— | CH=CH | (CH$_2$)$_2$((4-F-1,2-phe)C(Me)$_2$OH | SCH$_2$CH(CH$_3$)CH$_2$Tz |
| 26 | R | 5-CF$_3$CH$_2$CH$_2$ | 6-EtO | CH=CH | (CH$_2$)$_2$(4-Cl-1,2-phe)C(Me)$_2$OH | OCH$_2$C(CH$_3$)$_2$CH$_2$CO$_2$H |
| 27 | RS | 5-i-Pr | 6-MeOCH$_2$ | CH=CH | (CH$_2$)$_2$(4-Cl-1,2-phe)C(Me)$_2$OH | OCH$_2$CH(CH$_3$)CH$_2$Tz |
| 28 | RS | 3-F | 6-c-PrSCH$_2$ | CH$_2$O | (CH$_2$)$_2$(4-F-1,2-phe)C(Me)$_2$OH | SCH$_2$CH(C$_2$H$_5$)CH$_2$CONME$_2$ |
| 29 | S | 5-c-Pr | 6-Me | CH$_2$CH$_2$ | CH$_2$(4-F-1,2-phe)CMePhOH | SCH$_2$CH$_2$CO$_2$H |
| 30 | R | | 5,6-(CH$_2$)$_6$- | CH$_2$CH$_2$ | (CH$_2$)$_2$(3-Cl-1,2-phe)CHMeOH | SCH$_2$CH$_2$CONHS(O)$_2$Ph |
| 31 | R | | 5,6-CH$_2$CH$_2$CH(Me)— | CH$_2$S | (CH$_2$)$_2$(5-F-1,2-phe)CMeCF$_3$OH | SCH$_2$CH$_2$CONHS(O)$_2$CH$_3$ |
| 32 | RS | 5-MeOCH$_2$ | 6-EtSCH$_2$ | CH=CH | (6-CF$_3$-1,2-phe)CHCF$_3$OH | SCH$_2$CH$_2$CONHS(O)$_2$CF$_3$ |
| 33 | R | 5-Me | 6-C$_3$H$_5$ | CH$_2$O | (CH$_2$)$_2$(4-CF$_3$-1,2-phe)C(CF$_3$)$_2$OH | SCH$_2$C(CH$_2$)$_2$CH$_2$CONHS(O)$_2$Ph |
| 34 | R | 5-i-C$_3$H$_5$ | 6-Me | CH=CH | (CH$_2$)$_2$(4-F-1,3-phe)CMeEtOH | SCH$_2$CH$_2$C(CH$_3$)$_2$CO$_2$H |
| 36 | S | 5-Cl | 6-CF$_3$CH$_2$CHMe | CH=CH | (CH2)$_2$(4-F-1,2-phe)C(CH$_2$)$_3$OH | SCH$_2$C(CH$_2$)$_2$NHS(O)$_2$CF3 |
| 37 | R | 4-F | 5,6-(CH$_2$)$_4$ | CH$_2$S | (CH$_2$)$_2$(4-F-1,2-phe)C(CH$_2$)$_4$OH | SCH$_2$C(CH$_2$)$_3$CH$_2$CO$_2$H |
| 38 | R | 3-MeO | 5-(CF$_3$)$_2$CHCH$_2$ | CH=CH | (CH$_2$)$_2$(4-F-1,2-phe)C(CH$_2$)$_5$OH | SCH$_2$C(CH$_2$)$_4$CH$_2$CO$_2$H |

4. A pharmaceutical composition comprising a therapeutically effective amount of a compound of claim 1 and a pharmaceutically acceptable carrier.

* * * * *